(12) United States Patent
Larkin et al.

(10) Patent No.: US 11,078,454 B2
(45) Date of Patent: *Aug. 3, 2021

(54) BIOREACTOR AND METHOD OF FORMING COMPLEX THREE-DIMENSIONAL TISSUE CONSTRUCTS

(71) Applicant: The Regents of the University of Michigan, Ann Arbor, MI (US)

(72) Inventors: Lisa M. Larkin, Ann Arbor, MI (US); Ellen M. Arruda, Ann Arbor, MI (US); Michael J. Smietana, Ann Arbor, MI (US); Pablo Moncada-Larrotiz, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 159 days.

This patent is subject to a terminal disclaimer.

(21) Appl. No.: 16/197,944

(22) Filed: Nov. 21, 2018

(65) Prior Publication Data

US 2019/0153375 A1 May 23, 2019

Related U.S. Application Data

(63) Continuation of application No. 15/211,501, filed on Jul. 15, 2016, now Pat. No. 10,167,444.

(60) Provisional application No. 62/193,030, filed on Jul. 15, 2015.

(51) Int. Cl.
| | |
|---|---|
| *C12M 1/12* | (2006.01) |
| *C12M 1/42* | (2006.01) |
| *C12M 1/00* | (2006.01) |
| *C12M 1/24* | (2006.01) |
| *C12N 5/071* | (2010.01) |

(52) U.S. Cl.
CPC ............ *C12M 25/14* (2013.01); *C12M 23/04* (2013.01); *C12M 23/08* (2013.01); *C12M 23/34* (2013.01); *C12M 23/50* (2013.01); *C12M 29/10* (2013.01); *C12M 35/08* (2013.01)

(58) Field of Classification Search
None
See application file for complete search history.

(56) References Cited

U.S. PATENT DOCUMENTS

| | | | |
|---|---|---|---|
| 6,207,451 | B1 | 3/2001 | Dennis et al. |
| 6,796,977 | B2 * | 9/2004 | Yap ............................ A61F 2/08 600/36 |
| 7,338,798 | B2 | 3/2008 | Dennis et al. |
| 8,097,455 | B2 | 1/2012 | Larkin et al. |
| 8,147,562 | B2 | 4/2012 | Vacanti et al. |
| 8,546,142 | B2 | 10/2013 | Martin et al. |
| 8,709,793 | B2 | 4/2014 | Taboas et al. |
| 8,764,828 | B2 * | 7/2014 | Arruda ...................... A61F 2/28 623/13.17 |
| 2004/0014205 | A1 | 1/2004 | Banes |
| 2004/0126405 | A1 | 7/2004 | Sahatjian et al. |
| 2006/0194320 | A1 | 8/2006 | Bushnaq-Josting et al. |
| 2006/0292690 | A1 | 12/2006 | Liu et al. |
| 2008/0194010 | A1 | 8/2008 | Liu |
| 2009/0191631 | A1 | 7/2009 | Bornemann |
| 2010/0075293 | A1 | 3/2010 | Chang et al. |
| 2010/0273253 | A1 | 10/2010 | Teixeira De Oliveria et al. |
| 2011/0033918 | A1 * | 2/2011 | Asnaghi ................. C12M 23/34 435/289.1 |
| 2011/0207175 | A1 * | 8/2011 | El-Sabban ............. C12M 29/04 435/70.3 |
| 2013/0131825 | A1 | 5/2013 | Ganey |
| 2014/0154662 | A1 | 6/2014 | Alavi et al. |
| 2015/0079584 | A1 * | 3/2015 | Gevaert ............... C12N 5/0062 435/6.1 |

OTHER PUBLICATIONS

Abbasalizadeh, S. et al., "Technological Progress and Challenges Towards cGMP Manufacturing of Human Pluripotent Stem Cells Based Therapeutic Products for Allogeneic and Autologous Cell Therapies", Biotechnology Advances (2013), vol. 31, pp. 1600-1623.

Archer, R. et al., "Why Tissue Engineering Needs Process Engineering", Nature Biotechnology (2005), vol. 23 No. 11, pp. 1353-1355.

Bouchie, A, "Tissue Engineering Firms Go Under", Nature Biotechnology (2002), vol. 20, pp. 1178-1179.

Davie, N.L. et al., "Streamlining Cell Therapy Manufacture", BioProcess International (2012), vol. 10 No. 3, pp. 24-26, 28, 49.

Goltry, K. et al., "Large-Scale Production of Adult Stem Cells for Clinical Use", Emerging Technology Platforms for Stem Cells (2009), pp. 153-168.

Lysaght, M.J. et al., "Tissue Engineering: The End of the Beginning", Tissue Engineering (2004), vol. 10 No. 1/2, pp. 309-320.

Lysaght, M.J. et al., "Great Expectations: Private Sector Activity in Tissue Engineering, Regenerative Medicine, and Stem Cell Therapeutics", Tissue Engineering: Part A (2008), vol. 14 No. 2, pp. 305-314.

Ma, J. et al., "Three-Dimensional Engineered Bone-Ligament-Bone Constructs for Anterior Cruciate Ligament Replacement", Tissue Engineering: Part A (2012), vol. 18 No. 1 and 2, pp. 103-116.

Marston, W.A. et al., "The Efficacy and Safety of Dermagraft in Improving the Healing of Chronic Diabetic Foot Ulcers: Results of a Pospective Randomized Trial", Diabetes Care (2003), vol. 26 No. 6, pp. 1701-1705.

(Continued)

*Primary Examiner* — Nghi V Nguyen
(74) *Attorney, Agent, or Firm* — Reising Ethington P.C.

(57) ABSTRACT

A bioreactor and method of forming complex three-dimensional tissue constructs in a single culture chamber. The bioreactor and methods may be used to form multi-phasic tissue constructs having tissue formed from multiple cell types in a single culture chamber. The bioreactor includes at least one translation mechanism to facilitate translation of one or more tissue constructs without direct user intervention, thereby providing a closed, sterile environment for complex tissue fabrication. The bioreactor may be used as a stand-alone device or as part of a large-scale system including many bioreactors. The large-scale system may include a perfusion system to monitor and regulate the tissue culture environment.

18 Claims, 25 Drawing Sheets

(56) References Cited

OTHER PUBLICATIONS

Martin, I. et al., "Manufacturing Challenges in Regenerative Medicine", Science Translational Medicine (2014), vol. 6, pp. 1-3.
Ratcliffe, E. et all., "Current Understanding and Challenges in BioProcessing of Stem Cell-based Therapies for Regenerative Medicine", British Medical Bulletin (2011), vol. 100, pp. 137-155.
Rayment, E.A. et al., "Concise Review: Mind the Gap: Challenges in Characterizing and Quantifying Cell and Tissue Based Therapies for Clinical Translation", Stem Cell (2010), vol. 28, pp. 996-1004.
Dos Santos, F.F. et al., "Bioreactor Design for Clinical Grade Expansion of Stem Cells", Biotechnology Journal (2013), vol. 8, pp. 644-654.
Shaw, R, "Industrializing Stem Cell Production", BioProcess International (2010), pp. 10-15.
Wang, T. et al., "Bioreactor Design for Tendon and Ligament Engineering", Tissue Engineering: Part B (2012), vol. 19 No. 2, pp. 133-146.
Wendt, D. et al., "Potential and Bottlenecks of Bioreactors in 3D Cell Culture and Tissue Manufacturing", Advanced Materials (2009), vol. 21, pp. 3352-3367.
Williams, D.J. et al., "Tissue Engineering and Regenerative Medicine: Manufacturing Challenges", IEE Proc. Nanobiotechnol (2005), vol. 152 No. 6, pp. 207-210.
Williams, D.J. et al., "Precision Manufacturing for Clinical Quality Regenerative Medicines", Philosophical Transactions of the Royal Society A (2012), vol. 370, pp. 3924-3949.
Williams, D.J, "Overcoming Manufacturing and Scale Up Challenges", Regenerative Medicine (2011), vol. 6, pp. 67-69.

\* cited by examiner

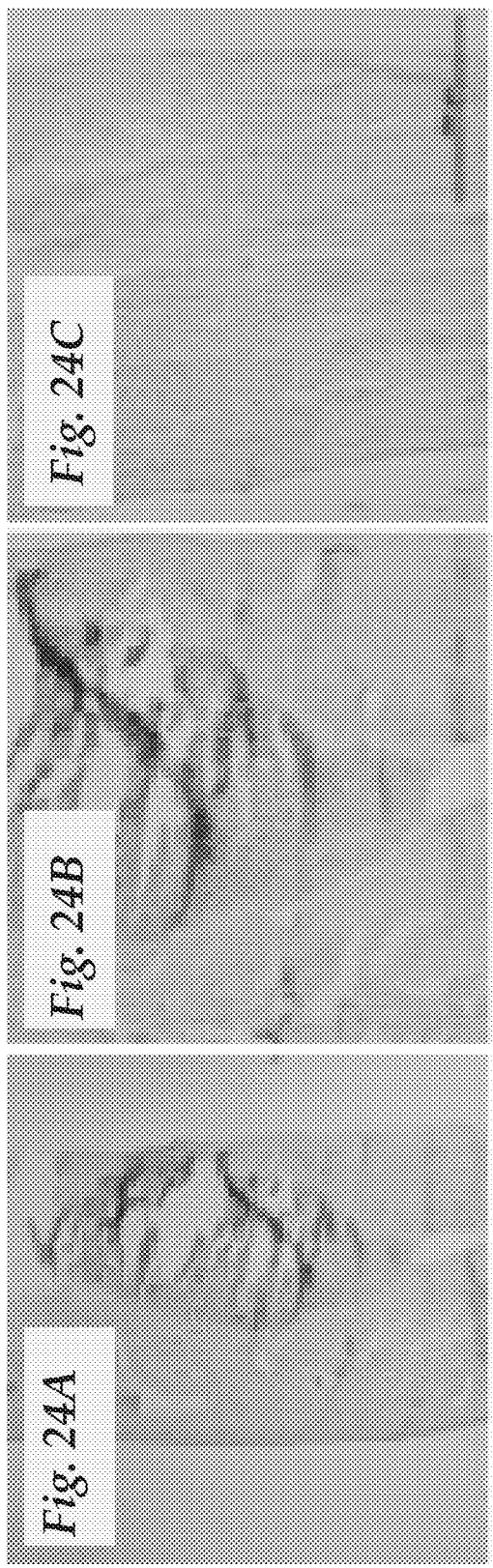
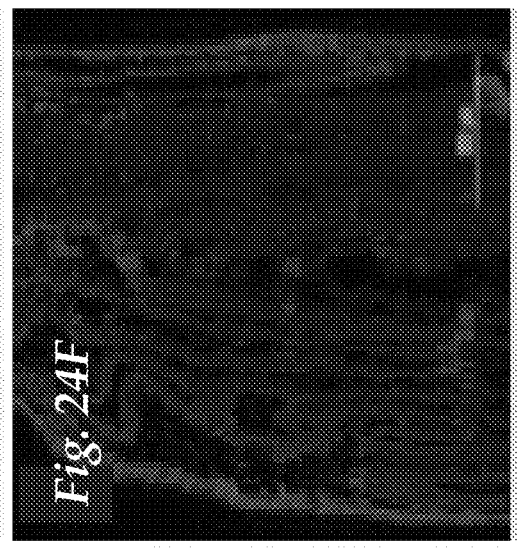
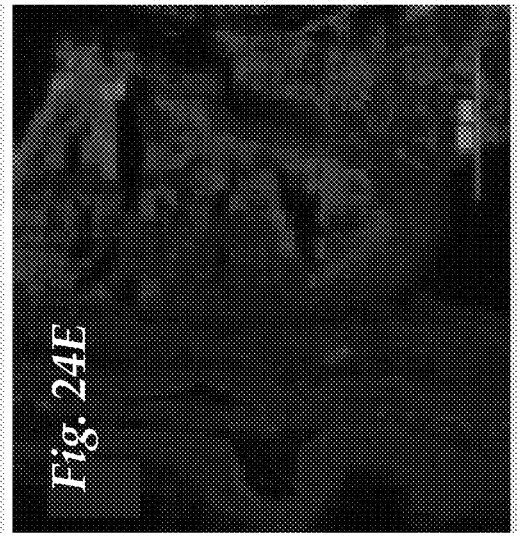
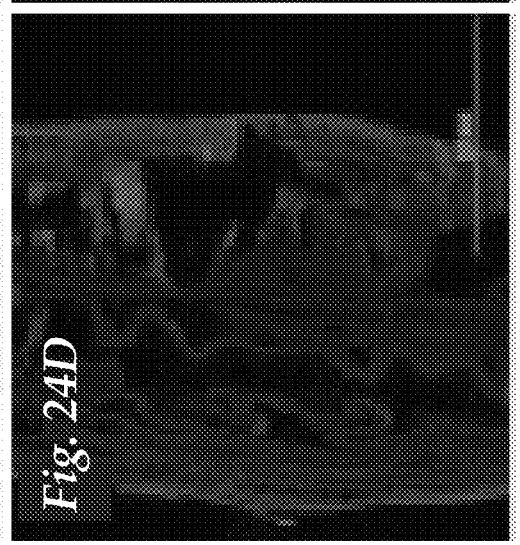

BIOREACTOR AND METHOD OF FORMING COMPLEX THREE-DIMENSIONAL TISSUE CONSTRUCTS

CROSS-REFERENCE TO RELATED APPLICATIONS

This application is a continuation of U.S. application Ser. No. 15/211,501 filed Jul. 15, 2016 which claims the benefit of U.S. Provisional Application No. 62/193,030 filed Jul. 15, 2015. The entire contents of each of these prior applications are hereby incorporated by reference.

TECHNICAL FIELD

This invention relates generally to bioreactors, and more particularly to bioreactors that facilitate the formation of complex three-dimensional and multi-phasic tissue constructs.

BACKGROUND

While advances in regenerative medicine have flourished, significant hurdles remain with respect to the commercial manufacture of consistent, uniform, reproducible tissue constructs. Relatively few products have realized commercial success as tissue substitutes despite significant advancements in the field of tissue engineering. Several challenges still remain for translating tissue-engineering technologies from bench to bedside. In addition to demonstrating clinical effectiveness, cost-effective manufacturing processes that comply with current quality and safety regulations are desirable. Failure to adequately consider the likely cost of manufacturing early in process and product development has been recognized as a limiting factor for commercial success of technologies in the field. Traditional manual laboratory tissue culture techniques are not economical at large clinical scales and have inherent variability and contamination risks. However, due to their widespread use, simplicity, minimal development time and low initial costs, these processes are often used to advance engineered tissues into clinical trials and the marketplace.

For example, CARTICEL, available from Aastrom Biosciences, Inc. (Ann Arbor, Mich.), is an autologous cell transplantation product used to repair articular cartilage injuries in the knee. CARTICEL is manufactured via manual techniques performed by trained technicians in a serologic clean room. Briefly, cells are isolated from the patient and expanded on tissue culture flasks to a sufficient number necessary for the desired therapeutic use. This process requires a large number of manual labor-intensive manipulation steps. Manual processes such as this, though perhaps more feasible and economical on a small-scale during early process development, are generally regarded as high risk due to the increased potential for contamination. Additionally, inherent differences in processing techniques between individuals, especially with technically challenging methods, can lead to process inconsistencies and end product variability. Furthermore, as production demand increases, scale-up would require multiple manual processes to be performed in parallel, thereby requiring additional technicians and generating substantial labor costs. As a result, the overall cost of production of such products tends to be high and can limit clinical success when the cost-benefit of the product is evaluated against competing, and often-simpler therapeutic strategies. Automating manual tissue-culture processes through use of bioreactor systems can provide a means to standardize culture processes, tightly control culture environments, remove user-dependent operation, and enable cost-effective tissue manufacturing processes to meet large-scale clinical demand.

Automated bioreactors have previously been used in tissue-engineering manufacturing and typically involve streamlining traditional two dimensional cell culture processes (e.g., cell selection, expansion, differentiation, etc.). While important, these cell manufacturing processes are often only the starting point for many tissue engineering strategies that utilize well characterized cell populations for tissue growth. Thus, there is a need to foster automated bioreactor-based systems fit for the development of reproducible three dimensional constructs. A closed, standardized, and operator-independent bioreactor system would have the potential to ensure safety and regulatory compliance and enable cost-effective, large-scale, in vitro tissue production.

Recently, Advance Tissue Science developed an automated system for large scale manufacturing of their human fibroblast derived dermal substitute, DERMAGRAFT (currently manufactured by Organogenesis, Inc. (Canton, Mass.)). DERMAGRAFT consists of living cryopreserved allogeneic dermal fibroblasts seeded onto a bio-absorbable polyglactin mesh scaffold used for treatment of chronic skin wounds such as diabetic foot ulcers. The entire manufacturing process is performed in a closed bioreactor bag, eliminating user-dependent variability and shielding the culture process from risk of contamination. Following injection of cells into the system, the bioreactor is only externally manipulated, until the graft is thawed and utilized in the operating room.

A single DERMAGRAFT bioreactor bag can be used to manufacture up to eight grafts, each in individual compartments. Additionally, twelve bags can be attached to an automated perfusion manifold system, standardizing culture parameters and allowing for up to 96 grafts to be made in a single production run. From a scientific perspective, the ability of an automated bioreactor system to systematically control and manipulate key culture parameters is important for providing data sets needed to standardize production methods and optimize end-product criteria. Though initial development costs of automated bioreactor systems are often high, the lack of user-dependence and ability to create large production volumes can greatly improve the long term cost effectiveness and commercial viability of the process. The lack of sufficient process control early in the DERMAGRAFT manufacturing process resulted in many defective products and ultimately contributed to overall high production costs. Thus, there is a need for process and manufacturing issues to be addressed earlier in product life cycle to increase likelihood of commercial success and clinical benefit. Failure to address manufacturing concerns early can lead to process changes later during pre-market approval that will likely require revalidation or additional studies to ensure safety and efficacy.

Current automated bioreactor systems such as the DERMAGRAFT are product specific and may pose problems for the fabrication of larger three-dimensional tissues. Moreover, no bioreactor currently exists for the fabrication of three-dimensional bone-ligament tissue constructs, such as those described in U.S. Pat. No. 8,764,828, assigned to the Applicant of the present application and hereby incorporated by reference in its entirety. To facilitate the manufacture of a wide-range of multi-phasic, three-dimensional tissue constructs, a novel bioreactor must be developed. As with current automated manufacturing systems, the bioreactor design should be user-independent, require only external manipulation, minimize contamination risk, and be scalable. It should also recreate the unique multi-step formation, technician-dependent processes often required when forming multi-phasic tissue constructs.

Transitioning the laboratory concepts and methods involved with the manufacture of multi-phasic tissue constructs into well-characterized medical products and processes is a significant challenge, commonly underestimated by researchers in tissue engineering and regenerative medicine fields. In addition to meeting regulatory requirements and ensuring the consistency and safety of the desired product, the manufacturing system must be scalable and cost-effective to be economically viable and displace current treatment options. Addressing manufacturing issues related to scale-out, quality control, and cost-effective production early in the research stage can overcome problems that typically slow development, limit investment, and escalate costs that limit the clinical translation and availability of various treatment methods to patients in need.

SUMMARY

According to one embodiment, there is provided a bioreactor for forming a complex three-dimensional tissue construct. The bioreactor comprises a first substrate for culturing a first cell source and a second substrate for culturing a second cell source. The first substrate and the second substrate comprise two walls of a culture chamber. The bioreactor further comprises at least one translation mechanism in the culture chamber extending at least partially between the first substrate and the second substrate so that a first tissue construct of the first cell source cultured on the first substrate or a second tissue construct of the second cell source cultured on the second substrate can be translated via the translation mechanism to form the three-dimensional tissue construct having the second tissue construct of the second cell source co-cultured with the first tissue construct of the first cell source.

According to another embodiment, there is provided a method of forming a multi-phasic tissue construct in a single culture chamber. The method comprises the steps of forming a first tissue construct in the culture chamber, adding cells to the culture chamber containing the first tissue construct, and culturing the cells to form a second tissue construct in the culture chamber. The first tissue construct and the second tissue construct are formed from different cell types and together comprise the multi-phasic tissue construct.

According to another embodiment, there is provided a method of forming a complex three-dimensional tissue construct in a single culture chamber. The method comprises the steps of adding cells from a first cell source to a first substrate in the culture chamber, adding cells from a second cell source to a second substrate in the culture chamber, culturing the first cell source and the second cell source to form a first tissue construct and a second tissue construct, translating the first and second tissue constructs via one or more translation mechanisms to a co-culture zone between the first and second substrates, and forming the three-dimensional tissue construct having the second tissue construct of the second cell source cultured with the first tissue construct of the first cell source.

BRIEF DESCRIPTION OF THE DRAWINGS

Preferred exemplary embodiments will hereinafter be described in conjunction with the appended drawings, wherein like designations denote like elements, and wherein:

FIGS. 24A-24F show histological staining results of multi-phasic tissue constructs formed in accordance with one embodiment.

DESCRIPTION OF THE ILLUSTRATED EMBODIMENTS

A bioreactor capable of producing complex three-dimensional tissue constructs, such as the bioreactor described herein, can promote the accessibility and availability of a diverse array of tissue constructs for various treatment and research purposes. Complex three-dimensional tissue constructs can include multiple tissue constructs formed from multiple cell sources, and more particularly, complex three-dimensional tissue constructs can include multi-phasic tissue constructs that include multiple tissue constructs cultured from cell sources with one or more of the cell sources containing different cell types (e.g., bone and ligament cells). The bioreactor can allow for cells of two different sources to be grown independently and then co-cultured to fabricate a scaffold-free, multi-phasic three-dimensional engineered tissue with two or more different types of tissue in the final product. The bioreactor can be a stand-alone culture plate or part of an assembly that comprises numerous bioreactors and an environmental control system or perfusion system, for example. The bioreactor can allow for the formation of continuous, multi-phasic tissue constructs without any internal manipulation by the technician, thereby minimizing contamination risk. In addition to minimizing contamination risk, a closed bioreactor system can precisely control and maintain the tissue culture environment. Tissue growth and development is highly responsive to environmental factors (pH, temperature, nutrient concentration, etc.), and as such, the entire fabrication process can impact the integrity of the final product. Thus, it is desirable if the process maintains a high level of control to meet the rigorous current good manufacturing practices (CGMP) standards required by the Food and Drug Administration (FDA) to ensure tissue safety and manufacturing consistency (see Chapter 21 of the Code of Federal Regulations). The bioreactor disclosed herein can facilitate such an improved fabrication process, and advantageously, the complex three-dimensional tissue construct can remain in a closed or partially closed environment until it is ultimately needed for patient or researcher use. Through the elimination of manual, user-dependent processes, the bioreactor and method facilitate an automated system and process that can eliminate user variability and that promotes tissue construct consistency. Tissue manufacturing times may be reduced, and production capacity may be increased. Further, the system may be modular, capable of incorporating multiple bioreactors into a larger centrally controlled assembly while, in some embodiments, maintaining a relatively small overall volume to minimize the space required to manufacture the tissue constructs.

Figure 1:
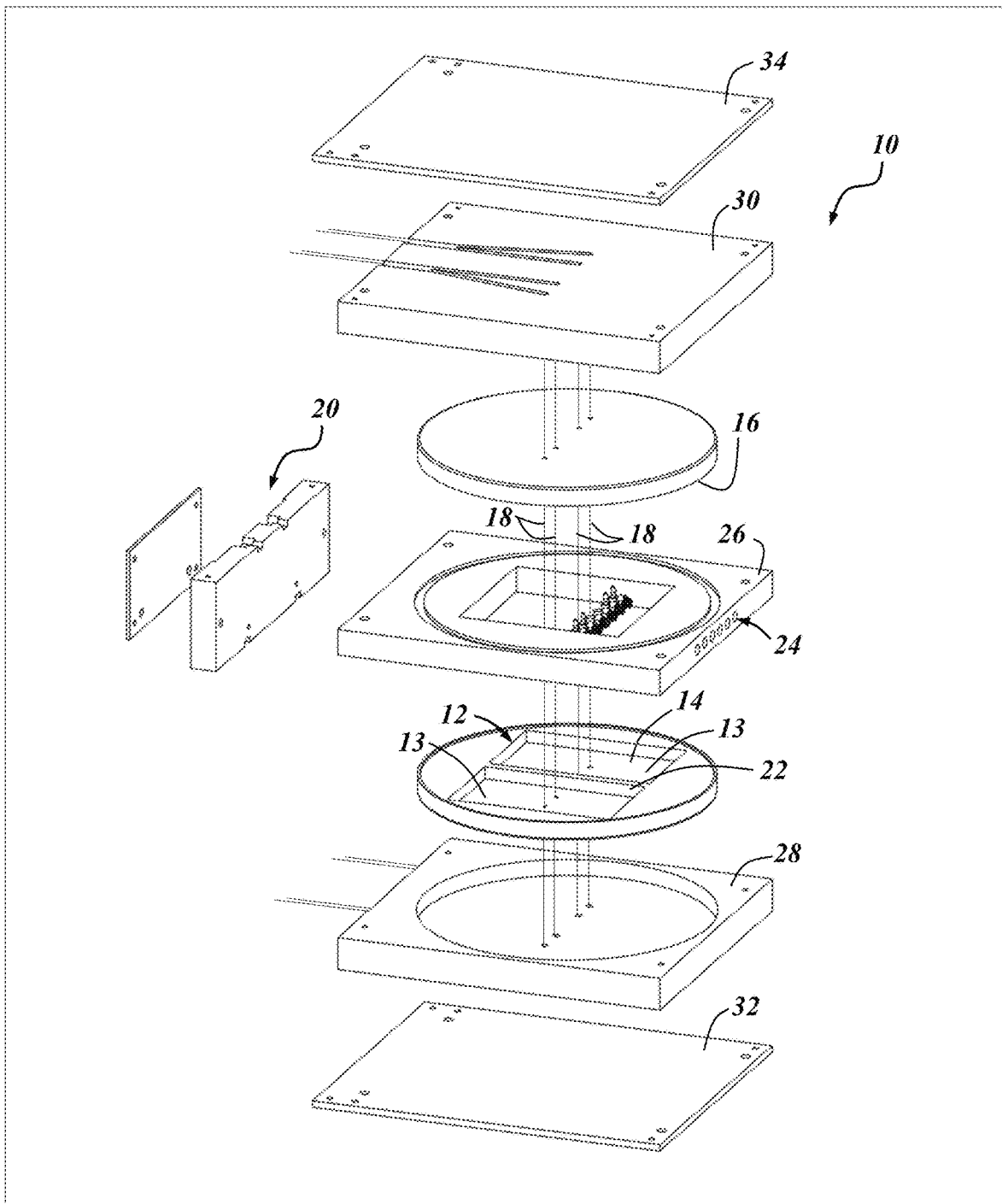
FIG. 1 is an exploded view of a bioreactor in accordance with one embodiment.
Figure 2:
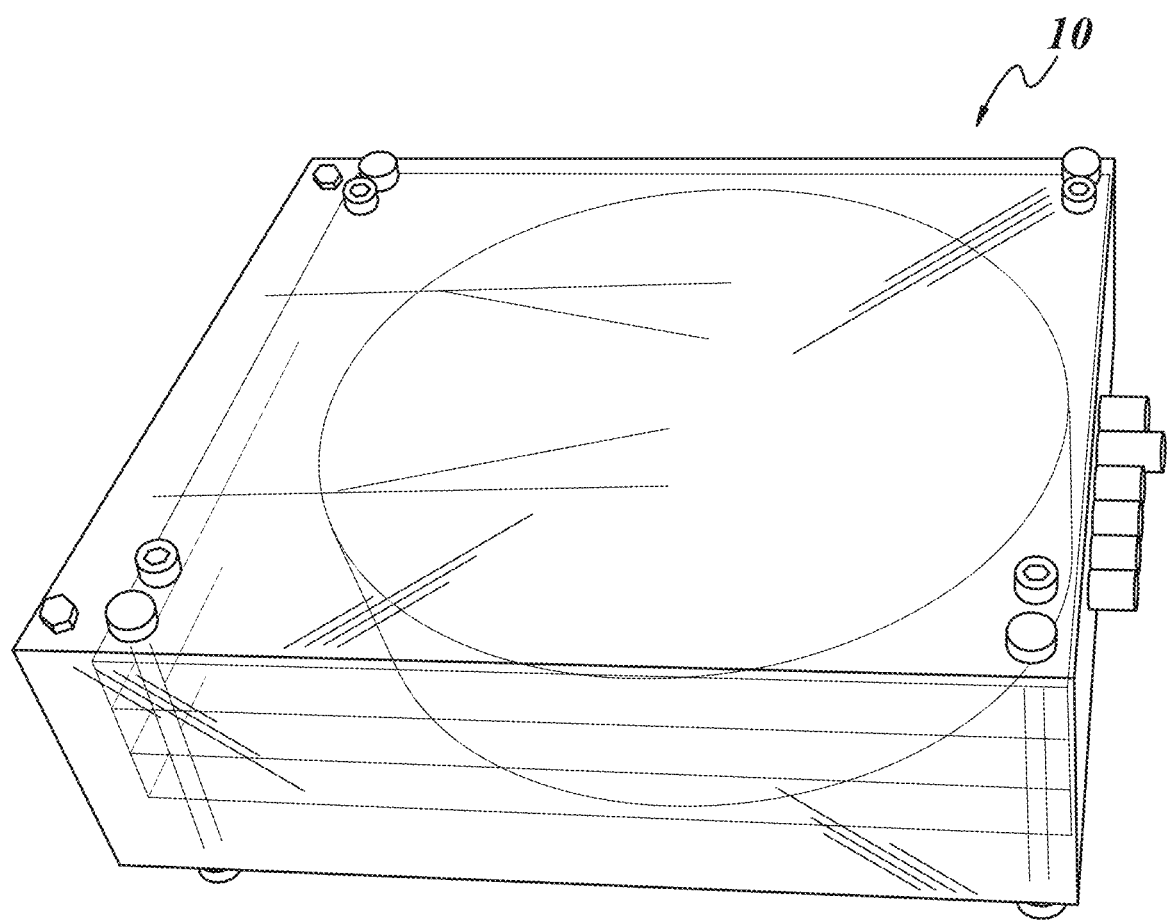
FIG. 2 shows a bioreactor in accordance with one embodiment.

FIG. 1 is an exploded view of one embodiment of a bioreactor 10 for forming one or more complex three-dimensional or multi-phasic tissue constructs, and FIG. 2 shows an assembled bioreactor in accordance with the FIG. 1 embodiment. Bioreactor 10 includes a culture chamber 12; however, it should be appreciated that more culture chambers may be included depending on the particular bioreactor design. The bioreactor includes a first substrate 14 for culturing a first cell source and a second substrate 16 for culturing a second cell source. The first substrate 14 and the second substrate 16 constitute two walls of the culture chamber 12, and in one embodiment, the substrates are constructed from a sterile polystyrene culture surface that may be coated with growth factors or cell adhesion proteins such as laminin. The addition of cell adhesion proteins can facilitate adherent cell culturing. The bioreactor further includes at least one translation mechanism 18 extending between the first substrate 14 and the second substrate 16, and in this embodiment, there are two sutures in each culture chamber 12 that constitute the translation mechanism 18. Translation component 20 may be included to help facilitate movement of the translation mechanism 18. Other translation mechanism embodiments are described in more detail below. A non-adherent barrier 22 may also be included to at least partially separate the culture chamber 12 into two culture vessels 13. Multiple culture vessels allow for the formation of multiple monolayers of various shapes and sizes. For example, two tissue constructs of the first tissue type may be formed, and then the bioreactor may be flipped, inverted, turned, or rotated so as to allow the second tissue construct of a second tissue type to form between the two tissue constructs of the first tissue type. If desired, the non-adherent barrier 22 may be made from silicone, TEFLON, or another material that does not allow for significant cell adhesion.

The bioreactor may further include ports 24 for exchanging various types of culture media. In the illustrated embodiment, ports 24 are located within a connecting plate 26 that is situated between the first substrate 14 and the second substrate 16. More or less ports may be included and may be integrated with other components of the bioreactor, depending on the particular design requisites. In one embodiment, the bioreactor includes a perfusion system (not shown) that is in communication with the ports 24 for temperature and/or fluid exchange, for example. Any standard perfusion system and control system can be used to monitor and control the conditions in and out of the bioreactor. In a preferred embodiment, the perfusion system includes pH, temperature, carbon dioxide, and oxygen level monitoring. A computer controlled system may run pumps that add and subtract culture media and record measurements from various sensors. The bioreactor 10 may be closed, using a perfusion system to control the internal environment, or it may be partially closed, leaving the ports 24 open to the external environment. Using a prototype bioreactor as shown in FIG. 2, which was partially closed, no contamination was observed, despite being slightly exposed to the external environment.

The bioreactor illustrated in FIGS. 1 and 2 may further include, but need not necessarily include, positioning plates 28, 30 for positioning the first and second substrates 14, 16, respectively, as well as cover plates 32, 34 for shielding various internal components of the bioreactor 10. Other plates, gaskets, fasteners, etc., may be included, as will be apparent to a skilled artisan. An optical load sensor could also be used in the bioreactor itself to help measure forces and facilitate removal of the graft.

The bioreactor 10 described herein was designed for the fabrication of scaffold-free bone-ligament-bone (BLB) multi-phasic tissue constructs. However, other cell types can be used, particularly those that form a spontaneously delaminating tissue monolayer or those that are capable of substrate controlled tissue monolayer delamination (e.g., muscle tissue, nerve tissue, etc.). Current cell culture bioreactors are typically designed for non-adherent cell suspension or cell expansion, but it should be understood that these devices do not provide the means of capturing and co-culturing delaminated monolayers of multiple tissue types required for the formation of multi-phasic tissue constructs, such as BLB tissue constructs.

Figure 3:
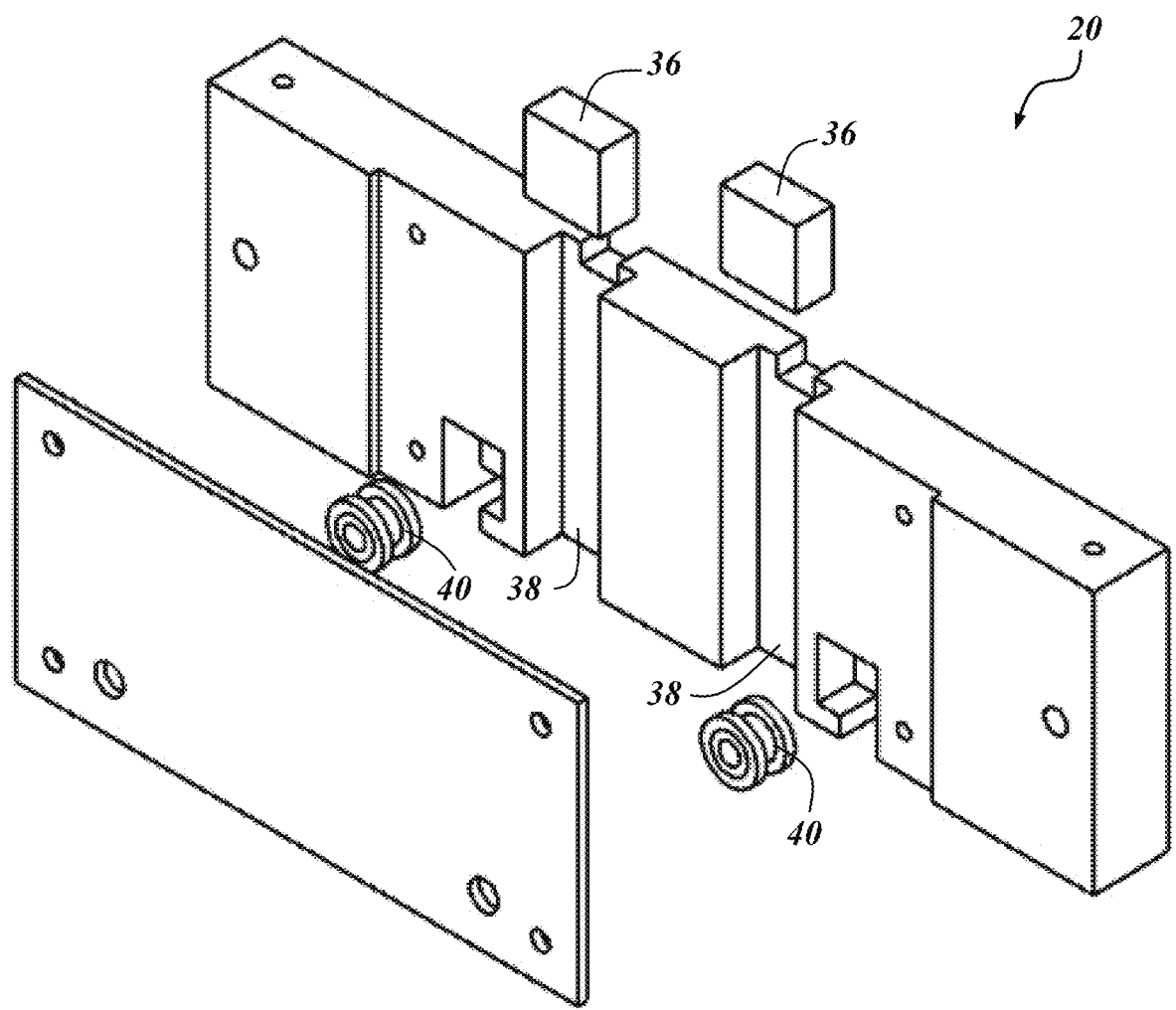
FIG. 3 is a perspective, exploded view of one embodiment of a component for a translation mechanism for a bioreactor.

With continued reference to FIG. 1, at least one translation mechanism 18 in the bioreactor 10 extends between the first substrate 14 and the second substrate 16 so that a first tissue construct of a first cell type cultured on the first substrate 14 can be translated to the second substrate 16 to form a multi-phasic tissue construct having a second tissue construct of the second cell type cultured with the first tissue construct of the first cell type. The translation mechanism 18 may be manual or automatic, so long as it is able to facilitate monolayer capture and transfer into co-culture. The translation mechanism may include any structure or device capable of facilitating translation of a tissue construct from one location in the bioreactor to another location. In the illustrated embodiment, the bioreactor 10 includes a pair of sutures as the translation mechanism. The sutures may be used for translation. During translation, the sutures may be controlled by the translation component 20, which is shown in an enlarged, exploded view in FIG. 3. In the translation component 20, magnets 36 move along grooves 38 to facilitate the lengthening or shortening of the translation mechanisms 18 as they are wound around anchoring spools 40. Manipulation of the position of the translation mechanisms 18 and the amount of tension may be used to control tissue construct length and graft tension for delaminated tissue constructs. In a preferred embodiment, a three-dimensional, first tissue construct is captured on the translation mechanisms 18 when the monolayer delaminates. The first tissue construct may be allowed to mature on the translation mechanisms 18, as the tissue contracts and reorganizes the extracellular matrix (ECM) structure while constrained under tension. This maturation phase may occur over approximately two days if a bone tissue construct is formed; however, longer or shorter maturation times are possible. To facilitate translation and co-culture of the first tissue construct, the bioreactor 10 may be inverted. Then, in this embodiment, following the release of tension in the translation mechanisms 18 by loosening the anchor spools 40, the first tissue construct can be translated to the second culture substrate 16 and tension may be re-established by pulling the magnets 36 after the anchoring spools 40 have been retightened.

Figure 4:
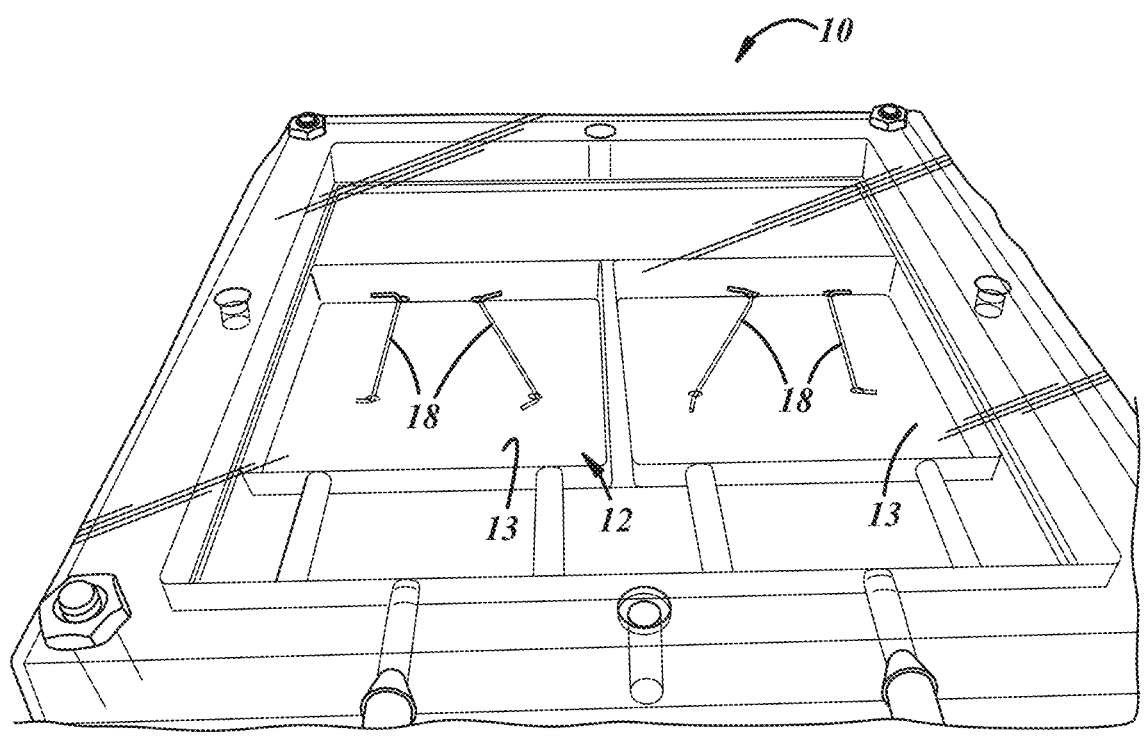
FIG. 4 is a top view of a bioreactor having a translation mechanism in accordance with one embodiment.

FIG. 4 is a top view of a bioreactor 10 that has a different embodiment for the translation mechanism 18. In this embodiment, the translation mechanism 18 is a pin or a post, and more particularly, a pair of pins in each of the two culture vessels 13. Since this translation mechanism 18 is rigid, as opposed to the sutures of the previous embodiment, a translation component that includes anchoring spools or other devices may not be necessary. As with the previous embodiment, the pins traverse the bioreactor 10, extending from the first substrate to the second substrate. In a preferred embodiment, the pins are angled relative to the substrates 14, 16. More particularly, the pins may be angled between 45° and 80° relative to the first substrate, and preferably the pins are angled 70° relative to the first substrate. Using a steep angle may allow the construct to translate faster. However, if the angle is too steep, the translation mechanisms may not allow enough tissue to form around the edges of the well, which may hinder contracting translation. In a further preferred embodiment, the pins are angled such that the distance between them is greater at the first substrate than at the second substrate. This allows for a first construct to slide up and shrink until it reaches the second substrate during translation. In one embodiment, after the first tissue construct reaches its position on the second substrate, the bioreactor 10 is flipped to seed cells on the second substrate that will delaminate and capture the first tissue construct, thereby forming a complex three-dimensional tissue construct or a multi-phasic tissue construct. The distance between the pins may be fixed depending on the specifications of the graft. In the embodiment illustrated in FIG. 4, the pins are spaced to form two 15 mm bone constructs in each culture vessel 13, and when the bioreactor 10 is flipped, a ligament tissue construct can form between the two bone constructs. The ligament tissue construct is approximately 50 mm, which generally equates to the distance between the two sets of pins.

Figure 5:
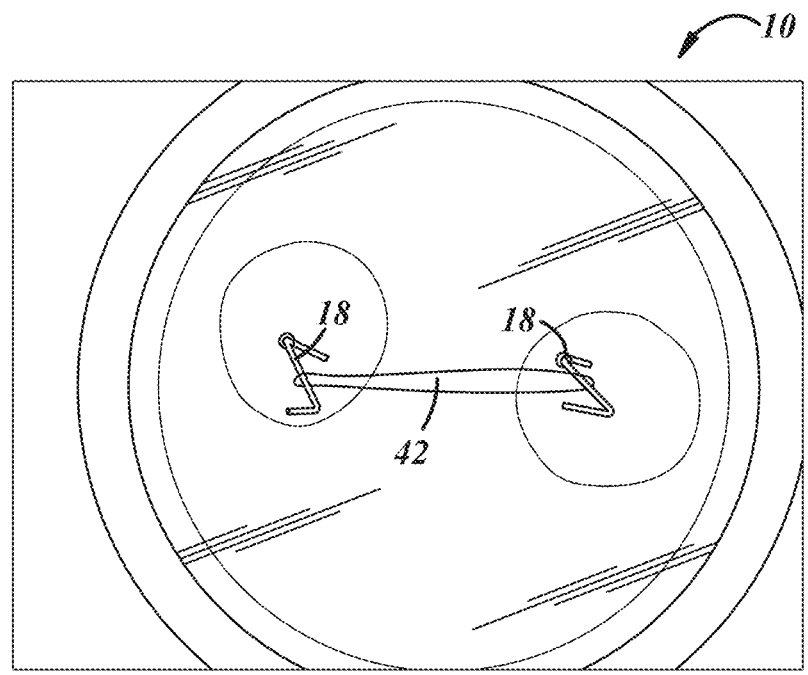
FIG. 5 illustrates a bioreactor in accordance with one embodiment.
Figure 6:
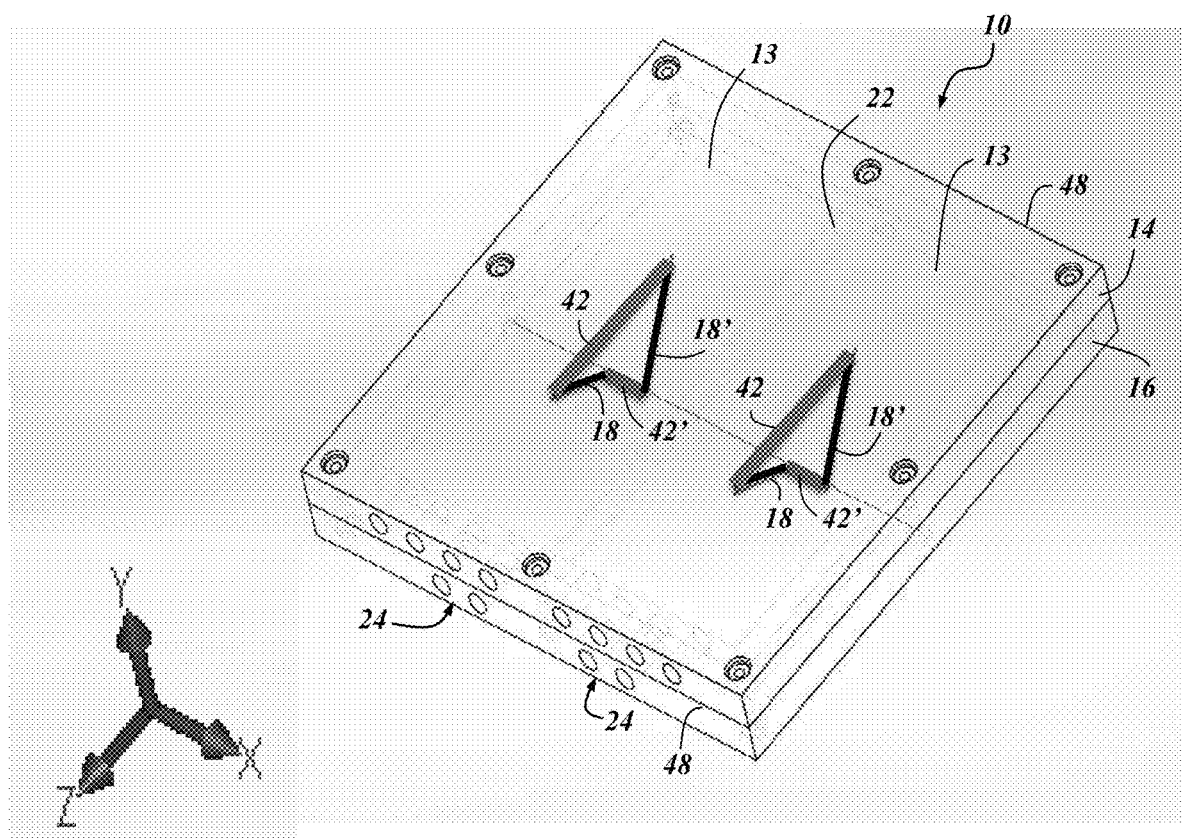
FIG. 6 is a perspective view of a bioreactor detailing the position of the translation mechanisms in accordance with one embodiment.

With reference to FIGS. 5 and 6, in addition to angling pins relative to the surfaces of the substrates 14, 16, one or more pins may be further angled relative to the sides 48 of the bioreactor. In other words, all of the pins may be angled relative to the y-axis of the plate toward the z-axis (e.g., by 70° relative to the surface of the first substrate 14), while the pins 18' are further angled relative to the x-axis toward the z-axis (e.g., up to 90° from its prior position). This allows for the first tissue construct 42 to shrink as it is translated, resulting in the first tissue construct 42' at the second substrate after delamination. These angles are merely exemplary and may be altered. Further, sides 48 of the bioreactor 10 and the x-, y-, and z-axes are provided as example reference points. Other reference points may certainly be used.

Figure 7:
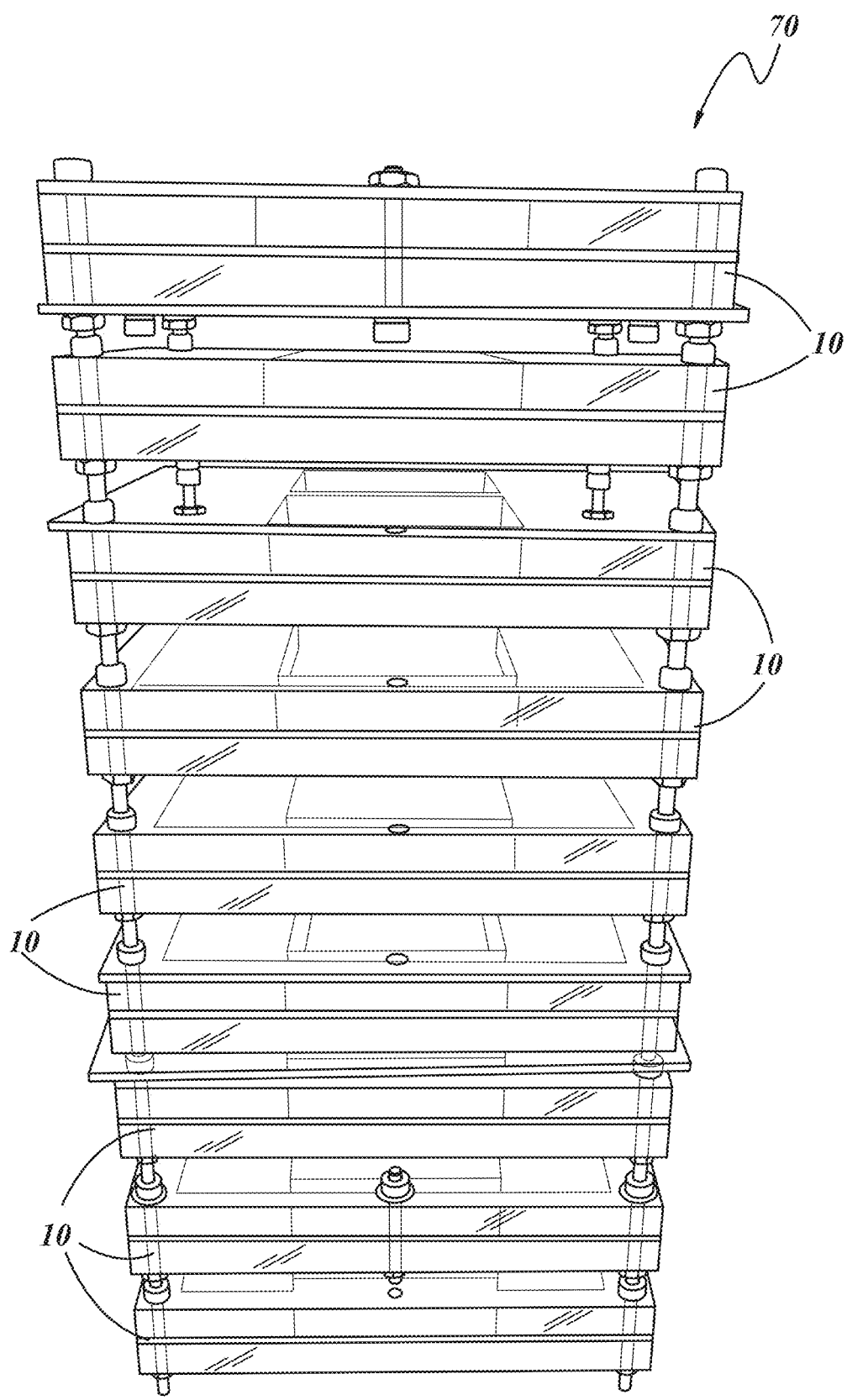
FIG. 7 shows an assembly of bioreactors in accordance with one embodiment.

FIG. 7 shows an assembly 70 that contains multiple bioreactors 10. The bioreactors may be similarly designed, or may have different designs, depending on the amount and/or types of tissue being formed. Further, as described above, the assembly 70 may be further equipped with a perfusion system to help control the culture environment. With a bioreactor assembly, several bioreactors may be connected in parallel to a single media reservoir and manifold system.

Preferably, the bioreactor 10 is fabricated from FDA compliant materials, and certain components of the bioreactor may be injection molded depending on the desired specifications of the bioreactor. The substrates 14, 16 may be disposable cell culture surfaces, and the rest of the bioreactor 10 may be sterilized using traditional sterilization techniques (e.g. autoclaving, ethylene oxide, etc.) and reused. Further UV treatment of the bioreactor 10 following assembly in a laminar flow hood, for example, can further ensure the sterility of the bioreactor prior to use. When fully closed, the bioreactor 10 can be used as a container for tissue preservation, storage, and shipping. Thus, the multi-phasic tissue construct can be preserved within the device so that it can be stored and opened when needed by the surgeon.

In addition to the bioreactor 10 and bioreactor assembly 70, there is also provided a method of forming a multi-phasic tissue construct in a single culture chamber. The method may comprise the steps of forming a first tissue construct in the culture chamber, adding cells to the culture chamber containing the first tissue construct, and culturing the cells to form a second tissue construct in the culture chamber. The first tissue construct and the second tissue construct can be formed from different cell types and together comprise the multi-phasic tissue construct. In another implementation, which is further detailed below with respect to another embodiment of a bioreactor 110, there is provided a method of forming a complex three-dimensional tissue construct in a single culture chamber. The method comprises the steps of adding cells from a first cell source to a first substrate in the culture chamber, adding cells from a second cell source to a second substrate in the culture chamber, and culturing the first cell source and the second cell source to form a first tissue construct and a second tissue construct. The first and second tissue constructs are translated via one or more translation mechanisms to a co-culture zone between the first and second substrates, and the three-dimensional tissue construct is formed and has the second tissue construct of the second cell source cultured with the first tissue construct of the first cell source.

Prior art methods for complex three-dimensional and multi-phasic tissue construct formation require simultaneous culture of both tissue constructs in separate culture chambers, and more particularly, BLB fabrication requires the simultaneous culture of bone and ligament monolayers in separate culture chambers. Forming the actual multi-phasic BLB graft requires the timed, manual transfer of two three-dimensional bone constructs onto a confluent ligament monolayer prior to the monolayer's delamination. The delicate timing and difficulty associated with manually performing this process can make it difficult to replicate in a closed bioreactor design. The sequential preparation of two tissue types such as bone and ligament tissues, in accordance with the methods described herein, would greatly eliminate the technical complexities of this process and simplify the bioreactor design. Thus, the ability to form a confluent, spontaneously delaminating ligament monolayer from a single fibrogenic cell suspension while in the presence of pre-formed bone constructs needed to be evaluated.

In order to test the viability of the methodology, the process of forming a single three-dimensional BLB construct of suitable diameter for use as a graft in ACL reconstruction in a single culture chamber was evaluated. Bone marrow was aspirated from the iliac crest of sheep using a MONOJECT Illinois needle (Sherwood Medical Company, St. Louis, Mo.) with the animal under general anesthesia induced by intravenous propofol and sustained with inhalation of isoflurane in oxygen. An exemplary minimum of 15 mL of bone marrow volume was collected using heparinized needles and dispensed into ethylenediaminetetraacetic acid (EDTA) blood collection tubes (BD, San Jose, Ca.) for processing. The marrow was filtered through a 110 mm filter to remove solid debris and consolidated into a single 50 mL conical. An equivalent volume of Dulbecco's Phosphate-Buffered Saline (DPBS) pH 7.2 (GIBCO BRL Cat#14190-144) was added. The marrow solution was slowly added to a 15 mL layer of FICOLL-PAQUE Premium (GE Healthcare, Munich, Germany) contained within a separate conical and centrifuged (ACCUSPIN FR; Beckman Coulter Inc., Fullerton, Calif.) at 600 g for 30 minutes @ 25 C. The upper layer containing plasma and platelets was discarded and mononuclear cell layers, containing the mesenchymal stem cell (MSC) population, were transferred into a new sterile conical. The cells were suspended in at least three times their volume of DPBS and centrifuged at 500 g for 10 minutes. The supernatant was removed and an equivalent volume of ammonium-chloride-potassium (ACK) lysis buffer was added to the pellet volume, lysing any remaining red blood cells. The conical was filled with DPBS and centrifuged at 400 g for 5 min. The supernatant was again removed and the MSC pellet was re-suspended in 20 mL of growth media (GM), which in this embodiment was Dulbecco's Modified Eagle Medium (DMEM) supplemented with 20% fetal bovine serum (FBS) and 2% fungizone (ABAM). Cells were counted utilizing a Countess automated counting system and plated at a density of 40 k cells/cm$^2$ in a 150 mm tissue culture dish.

The adherent cell population was allowed to attach for 3 days before the plate was rinsed with DPBS to remove any remaining debris or contaminating non-adherent cell populations. Following plating, cells were immediately cultured towards osteogenic or ligamentous lineages. The osteogenic growth medium consisted of GM supplemented with 600 ng/mL basic fibroblast growth factor (bFGF; PEPROTECH), 400 ng/ml dexamethasone (dex; Sigma-Aldrich). The ligamentous growth media consisted of GM supplemented with only bFGF. Plates were fed respective bone and ligament media every other day. At approximately 50% confluence the plate-adherent MSC populations were trypsinized (trypsin-0.25% EDTA), combined into a single conical, and passaged at a density of 5 k cells/cm' every other day. Following passage three, ligamentous derived MSCs (ligament cells) were trypsinized and cryogenically preserved. MSCs induced to a osteogenic lineage (bone cells) were passaged and cryopreserved after passage four. Cells were cryogenically preserved at a concentration of 5×10$^6$ cells/mL GM plus 10% dimethyl sulfoxide (DMSO) (Sigma-Aldrige). One mL volumes were aliquoted into 2 mL cryovials (Nalgene) and slowly frozen (approximately 1 C/hr) overnight to −80 C. The vial was then transferred into a liquid nitrogen freezer for long-term storage.

As needed, cells were removed from liquid nitrogen storage and placed in a 37 C water bath. After the media turned to liquid, the entire volume of cells and media was transferred to a sterile 15 mL conical containing at least 3 times their volume of warmed GM. The cell suspension was centrifuged at 1500 RPM for 5 min at 37 C. The supernatant was aspirated and remaining cells were re-suspended in fresh GM and counted. Cell viability was assessed with trypan blue dye (Life Technologies). Recovered cells utilized for tissue formation contained greater than 90% viable cells. Cells were seeded onto sterile polystyrene tissue culture plates at a viable cell density of 21 k cells/cm$^2$. Bone plates were fed GM supplemented with 400 ng/mL dex, 13 mg/mL ascorbic acid, 5 mg/mL L-proline, and 600 ng/mL bFGF. The ligament medium was similar to the GM, lacking only the dex.

Figure 8:
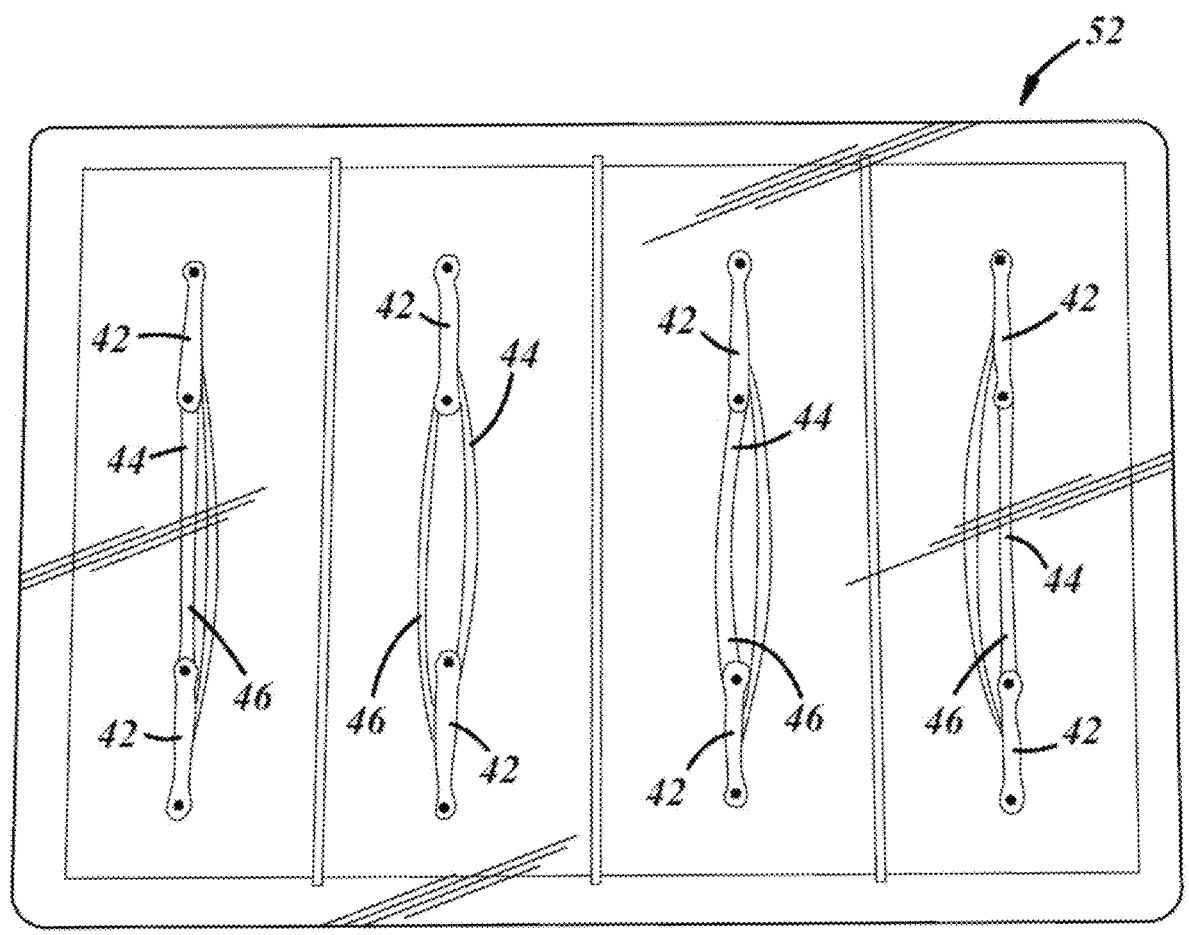
FIGS. 8-10 show multi-phasic tissue constructs formed in accordance with various embodiments.

With reference to FIG. 8, monolayers derived from both bone and ligament cryopreserved MSC lineages successfully formed and spontaneously delaminated, demonstrating the ability of cryogenically preserved cells to form BLB grafts. Additionally, seeding of ligament cells following transfer of bone constructs to the culture surface did not interfere with ligament monolayer formation required for successful co-culture and BLB formation. The delaminating ligament monolayers fully surrounded the bone constructs capturing them within the newly formed BLB construct. The diameter of the ligament region was noticeably thin (0.3±0.1 mm, n=5) with about half of the constructs failing in the ligament mid-substance after 2 weeks. The results demonstrate the ability to form a BLB sequentially in the same dish by first adding bone constructs before seeding ligament cells. Thus, as shown FIG. 8, a first tissue construct 42 of a first tissue type was successfully formed with a second tissue construct 44 of a second tissue type, thereby forming a multi-phasic tissue construct 46.

Figure 9:
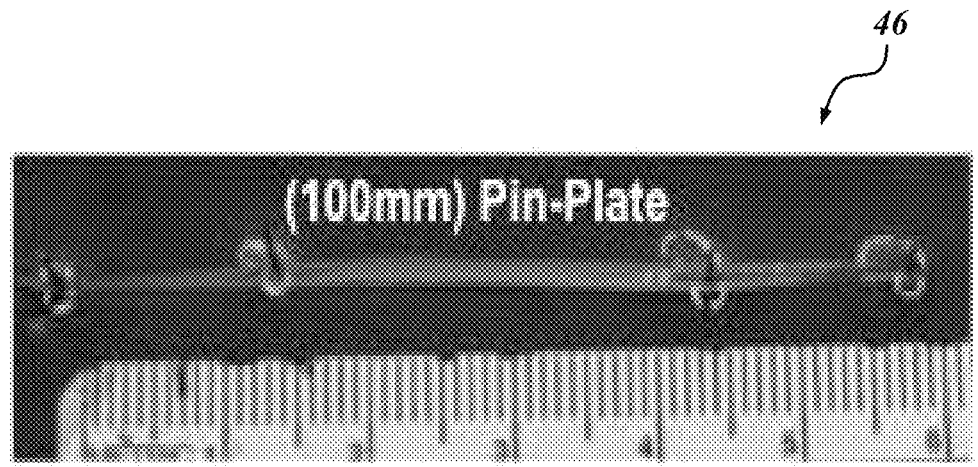
Figure 10:
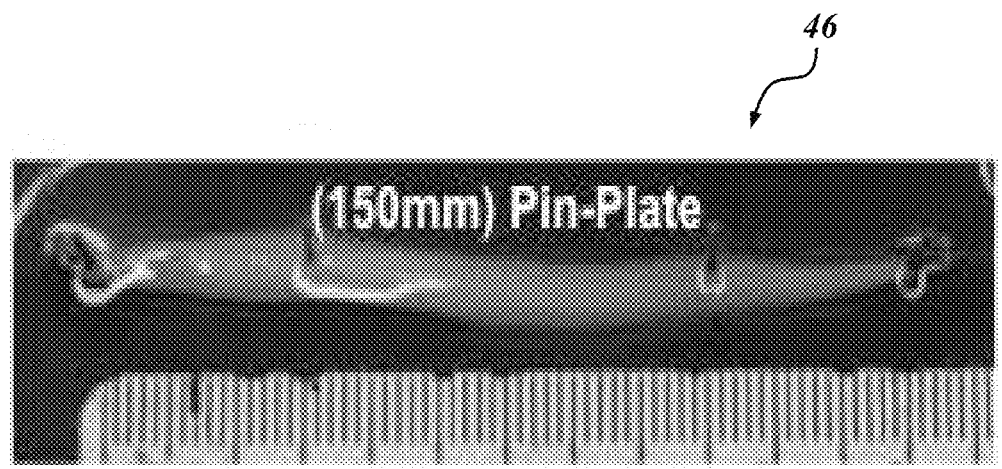

FIGS. 9 and 10 show other multi-phasic tissue constructs 46 that were formed in accordance with the methods described herein. Larger pin plates were fabricated utilizing 150 mm tissue culture plates, with a culture surface area of 182 cm$^2$. The plates included two metal pins or posts located 50 mm apart, which were centered and aligned uni-axially. As a control, 110 mm pin plates, with a culture surface area of 82 cm$^2$, were also fabricated. Pin locations were the same in each of the plates. Plates were UV treated for at least 1 hour and sprayed with 70% ethyl alcohol (ETOH) and rinsed with approximately 20 mL DPBS prior to use. Ligament cells were seeded onto 110 mm and 150 mm pin plates, grown into a confluent monolayer, and spontaneously delaminated into a three dimensional tissue construct. Construct diameters were compared at a one-week time point following delamination. FIG. 9 shows that the 110 mm pin-plate formed a construct approximately 2 mm in diameter (n=3), while FIG. 10 shows that constructs fabricated in the 150 mm pin-plates formed a construct about 5 mm in diameter (n=3).

Adding MSCs to individual wells containing strategically placed, pre-formed three-dimensional tissue constructs of a first tissue type, formed a multi-phasic construct. This is in sharp contrast to previous methodologies that required combination of three-dimensional tissue constructs of a first tissue type onto confluent monolayers of a second tissue type to form the multi-phasic tissue. The results demonstrate the feasibility to form a multi-phasic tissue construct, such as a BLB tissue construct, within a single well by sequentially seeding cryogenically preserved bone and ligament cells, for example. This process adaptation eliminates the need for technicians to combine bone and ligament tissues to form a BLB in this example. Cells, as opposed to three dimensional tissue constructs, can be added into the system, lending itself nicely for injection into a closed system. Elimination of technician dependent steps allows for the process to be automated and performed in a closed system, which is desirable for use within a bioreactor such as bioreactor 10.

The use of cryogenically preserved allogeneic cells can allow for large-scale expansion of cells that can be well characterized and used as needed for graft fabrication. This is a significant advantage for process scalability compared to fresh cells, as the starting cell population can be screened and evaluated before investing time and resources into large volume construct production. From a regulatory perspective, a well-defined starting cell population with specific acceptance criteria may be necessary. Allogeneic cells have the advantage of performing this characterization only once. Autogenic cells must be characterized for each donor and the resulting tissue constructs are patient specific. This can significantly increase the economy of scale and limit commercialization potential.

Additionally, the elimination of larger diameter grafts formed on the 150 mm plates compared to 110 mm plates, as shown in FIGS. 9 and 10, reveal the ability to control graft size through the manipulation of culture surface area. This process eliminates the need for manual fusion of multiple constructs by a technician, again, a technician-dependent step that can impede the development of efficient, automated manufacturing processes, thereby making the process suitable for incorporation with a bioreactor. The change of construct diameter, passive construct tension, and tissue mechanics should be evaluated further. The described results demonstrate protocol adaptations that were used to facilitate fabrication of a BLB construct within single well, closed, bioreactor system.

As alluded to above, the methods described herein may also be administered in a bioreactor, such as bioreactor 10. FIGS. 11A-11E schematically illustrate one embodiment of a method of forming a complex three-dimensional or multi-phasic tissue construct. While this embodiment of the method is shown as being performed with one particular design for the bioreactor 10, it should be understood that the method is not limited to use with the illustrated bioreactor, as any suitable bioreactor may be employed, such as bioreactor 10 shown in FIGS. 4-7 in this example. Method adjustments can be made for other bioreactor implementations, such as the bioreactor 110 depicted in FIG. 12, which is described in further detail below. Moreover, while the description below is provided with reference to the formation of a BLB multi-phasic tissue construct, other tissue types may be used and/or formed, such as those that form a spontaneously delaminating tissue monolayer or those that are capable of substrate controlled tissue monolayer delamination (e.g., muscle tissue, nerve tissue, etc.).

Figure 11A:
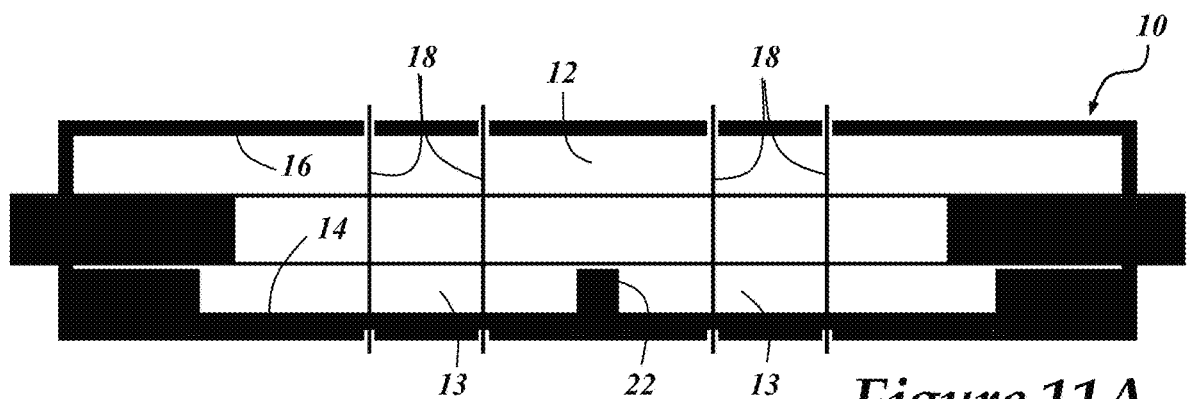
FIGS. 11A-11E illustrate various steps involved in one embodiment of forming a complex three-dimensional tissue construct.

FIGS. 11A-11E are schematic side views of bioreactor 10 having a first substrate 14 for forming a first tissue construct of a first cell type, and a second substrate 16 for forming a second tissue construct of a second cell type, which in this embodiment, is ligament tissue construct spanning two bone tissue constructs (i.e., a BLB multi-phasic tissue construct). Preferably, if forming a BLB construct, the bioreactor is kept at 37 C, 95% humidity and 5% $CO_2$ to allow for cell growth, with media exchange occurring within a sterile laminar flow hood. With reference to FIG. 11A, during bone monolayer formation, MSCs are seeded onto the first substrate 14, which preferably comprises a sterile polystyrene culture surface coated with or without cell adhesion proteins such as laminin. The MSCs may be induced towards an osteogenic lineage and sterilely delivered into individual culture vessels 13 within the culture chamber 12 of the bioreactor 10 and fed nutrients and growth factors specific to bone formation. Media exchange may be controlled manually with sterile injection of media in an open-environment or automatically with perfused media. MSCs of the bone monolayer growth process may be seeded at an initial density of approximately 21,000 cells/cm$^2$. Seeding density may not be critical to the success of forming a multi-phasic tissue construct, as it may only affect the rate of monolayer formation.

Figure 11B:
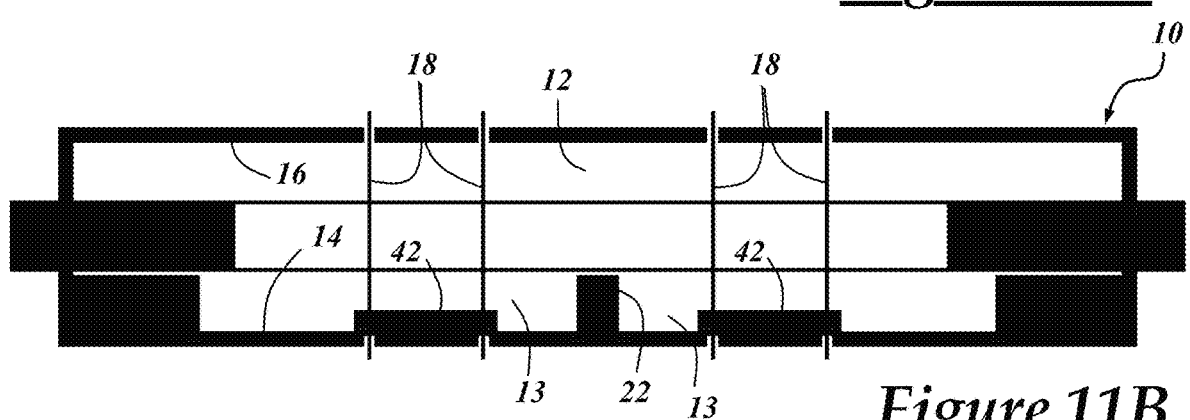

With reference to FIG. 11B, after seeding, cells proliferate forming a monolayer, and differentiate towards an osteogenic lineage. While additional serum-containing cell culture media and growth factors may be used, a preferred growth medium to optimize the cell proliferation and promote robust osteogenic ECM production consists of DMEM supplemented with 20% fetal bovine serum and antibiotics along with the addition of dex, fibroblast growth factor (FGF-b), and ascorbic acid/L-proline. Growth conditions that are preferable include a pH of about 7.4, a medium temperature of 37 C, and a sterile air environment consisting of up to 20% $CO_2$. Media should be exchanged at a sufficient rate and volume to prevent depletion of critical media constituents by the growing cells, with preferably 50% of the media volume being replaced every two days.

Figure 11C:
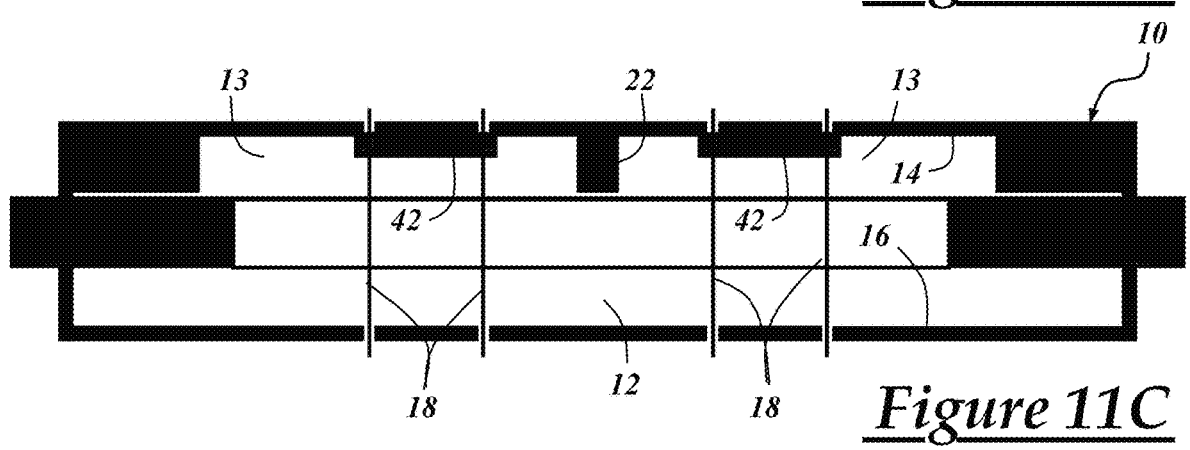
Figure 11D:
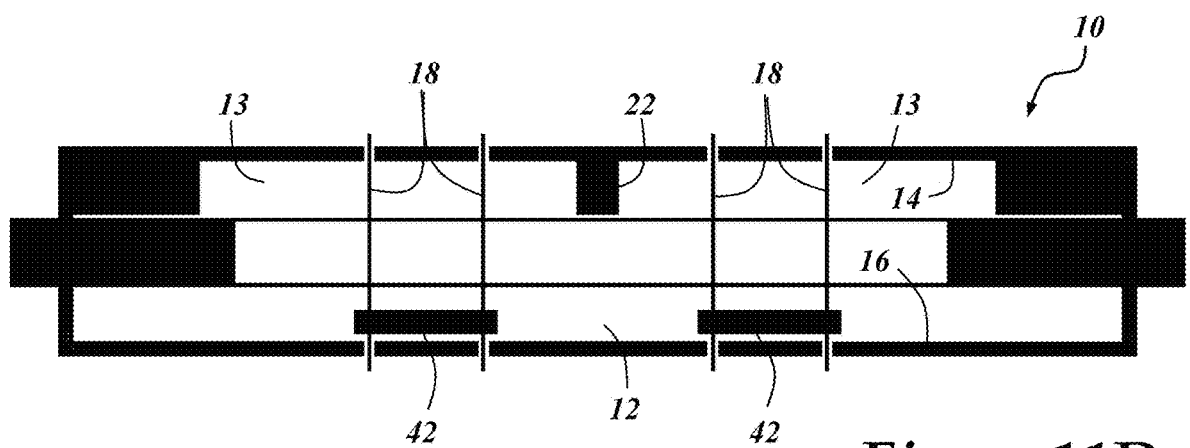

Following sufficient ECM matrix production by the seeded cells, a confluent bone monolayer is formed on the first substrate 14, which in one embodiment, occurred approximately 5 days at the described seeding density. Growth-promoting medium can be replaced with differentiation medium consisting of DMEM, supplemented with 7% horse serum, antibiotic, transforming growth factor-beta (TGF-b), ascorbic acid/L-proline, and dex to induce cell differentiation, integration and passive tension that leads to subsequent spontaneous delamination of a confluent tissue monolayer. Bone monolayer delamination within the culture vessel 12 may be captured on the translation mechanisms 18, forming a three dimensional bone tissue construct 42 as shown in FIG. 11B. The bone tissue constructs 42 may be allowed to mature on the translation mechanisms 18 as the tissue continues to contract and reorganize the ECM structure while constrained under tension. This maturation phase can occur over approximately 2 days; however, longer or shorter maturation times are possible. To facilitate translation and co-culture of the bone constructs 42, the bioreactor 10 may be inverted or flipped, as shown in FIG. 11C. Bioreactor inversion, and possibly the release of tension in the sutures depending on the particularities of the bioreactor being used, result in the translation of the bone tissue 42 to the second substrate or ligament substrate 16, as shown in FIG. 11D. Bioreactor inversion may be done by hand, by a technician for example, or it may be automated by a mechanical device. If a bioreactor assembly is being used, such as the bioreactor assembly 70 shown in FIG. 7, the entire assembly may be inverted or the assembly may be designed such that the bioreactors are individually inverted at various times.

Following translation of the bone constructs 42, MSCs are seeded onto the second substrate 16 at an initial density of approximately 21,000 cells/cm$^2$ in one example. The osteogenic medium may be replaced with ligament growth medium to promote fibroblastic differentiation and production of ligamentous ECM. This process can require approximately 8 days in culture. The ligamentous medium consists of DMEM supplemented with 20% fetal bovine serum and antibiotics along with the addition of FGF-b, and ascorbic acid/L-proline. Ligament medium may be exchanged at 50% of volume every 2 days. Other environmental conditions required for ligament tissue growth may be the same as for bone tissue growth.

Figure 11E:
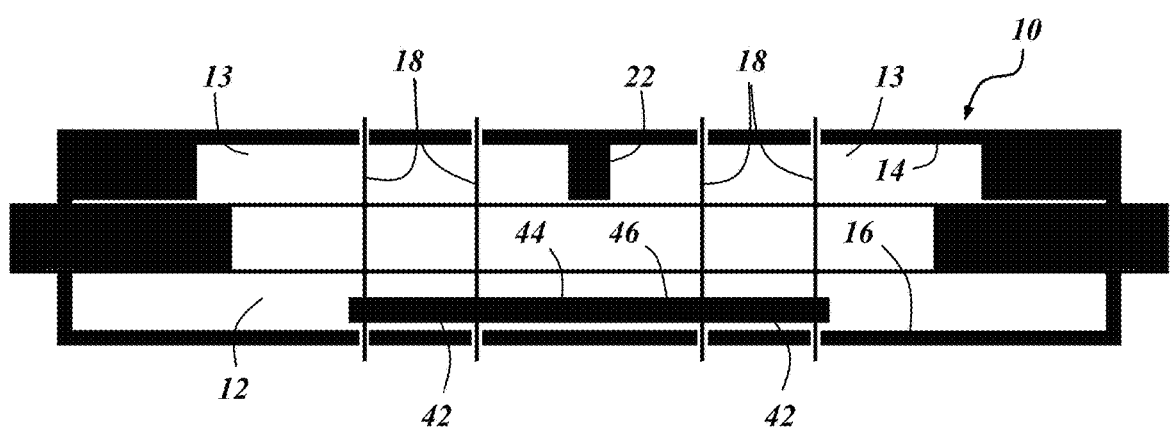

Following formation of a ligament monolayer upon the ligament culture substrate 16, the medium may be switched to differentiation medium to further induce matrix production and cell-matrix tension. The ligamentous differentiation medium may be composed of DMEM, supplemented with 7% horse serum, antibiotic, transforming growth factor-beta (TGF-b), and ascorbic acid/L-proline. As the ligament monolayer spontaneously delaminates forming the ligament tissue structure 44, the translation mechanisms 18 can capture it, surrounding the bone constructs 42 on the second substrate 16. The end result is a multi-phasic BLB construct 46 that may continue to mature (remodel, condense, and develop ECM) over time in culture, as shown in FIG. 11E. This maturation phase may require approximately 1 week, although shorter and longer periods are possible.

The resulting BLB construct 46 can be grafted into the patient at this point or if desired, further conditioned mechanically through the physical manipulation of the translation mechanisms 18, which are sutures in this embodiment. If implanted, the incorporated sutures may be utilized to secure the graft into the patient during the surgical procedure. This may be desirable for trans-osseous rotator cuff repair or anatomical ACL reconstructive surgery, where the multi-phasic tissue construct is sutured to the periosteum of the bone. If sutures are included during fabrication of the complex three-dimensional tissue construct, it is desirable if the sutures provide adequate material to secure the ends of the graft and anchor the multi-phasic tissue construct during surgery. Alternative suture configurations may be included to enhance suture-graft integration and provide additional stability during implantation and fixation to native tissue. It is preferable that a fresh BLB construct be used within 3 weeks following formation, as cells and appropriate graft tension are difficult to maintain in culture for extended periods of time. Alternatively, freezing, acellularizing, or other means of preservation may be used to preserve the construct.

The resulting multi-phasic tissue construct 46 was continuous, having compositionally different tissue at each end. A mineralized matrix was observed in the bone regions 42 of the graft despite the removal of dexamethasone and prolonged exposure to ligament growth medium. Further, it should be understood that the size of the multi-phasic tissue construct formed in a bioreactor may be slightly smaller than if produced according to other methods (e.g., 5 mm and 2 mm in diameter for 110 mm and 150 mm plates, respectively, versus 2-3 mm diameter for the bioreactor). However, the resulting tissue construct will likely grow in size in vivo to approximate the native tissue dimensions. Despite this, the in vitro construct should still maintain a consistent and robust diameter to provide sufficient structural integrity during the implantation procedure. Thus, strategies to maintain the multi-phasic tissue construct size, such as altering culture surface area, removing TGF-B, or releasing suture tension, for example, may be used to prevent excessive tissue condensation and better preserve construct diameter and viability. It is likely that inherent variability in cell ECM synthesis and remodeling was a factor in the size disparity.

Figure 12:
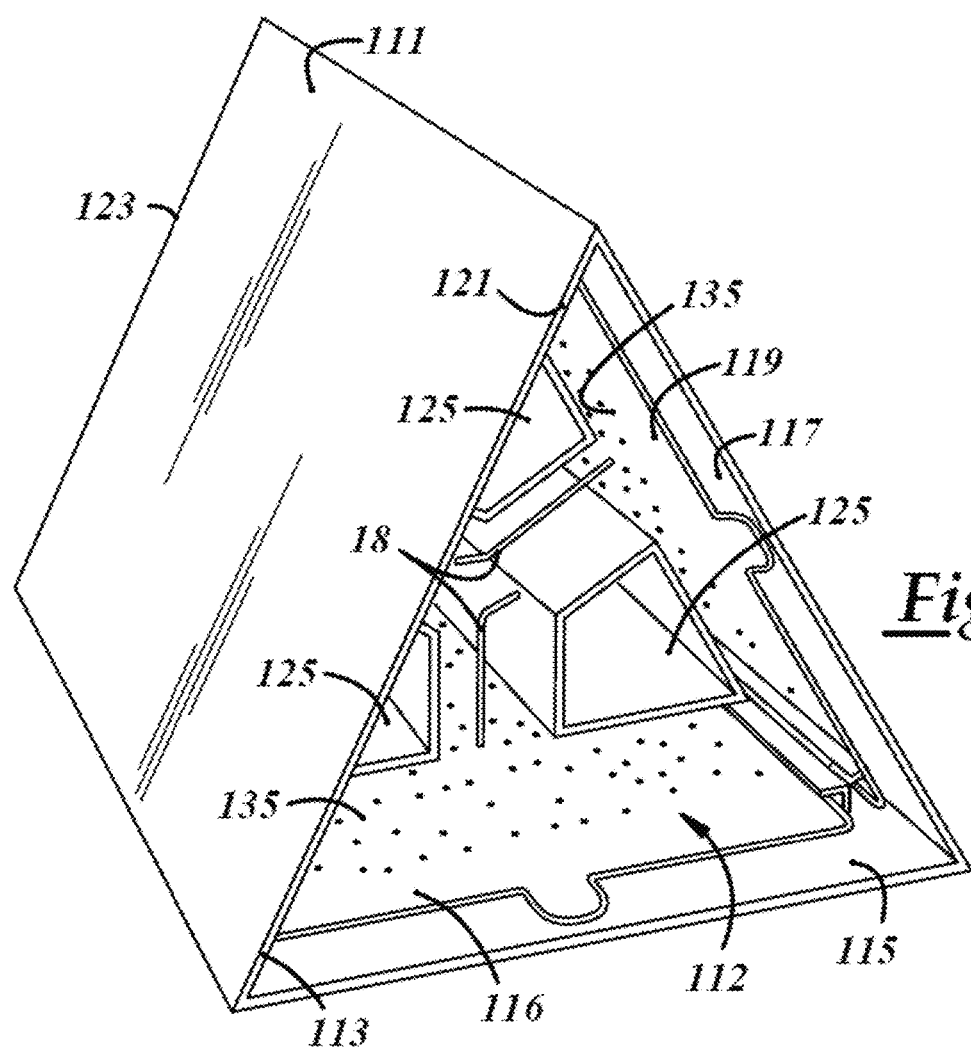
FIG. 12 is a perspective view of a bioreactor in accordance with one embodiment.
Figure 13A:
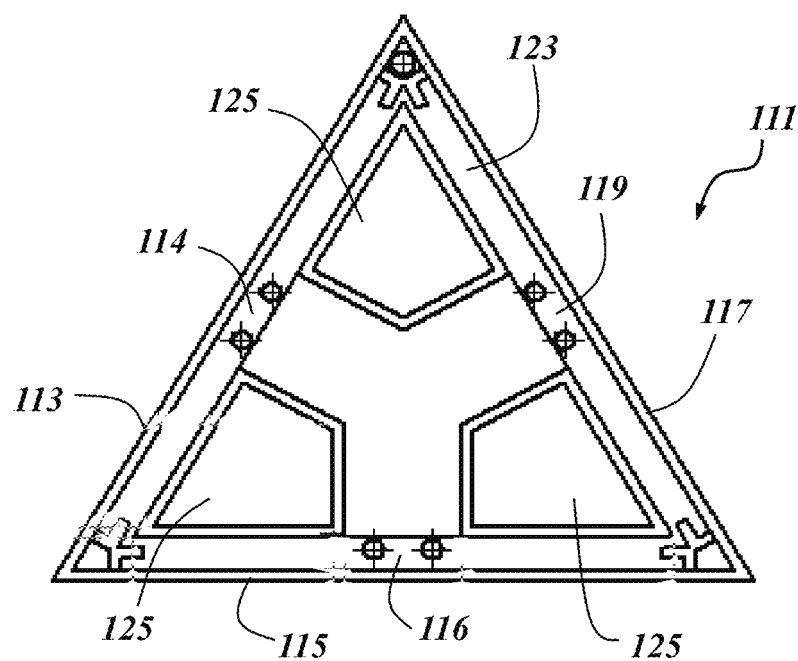
FIGS. 13A and 13B show various views of the body of the bioreactor shown in FIG. 12.
Figure 13B:
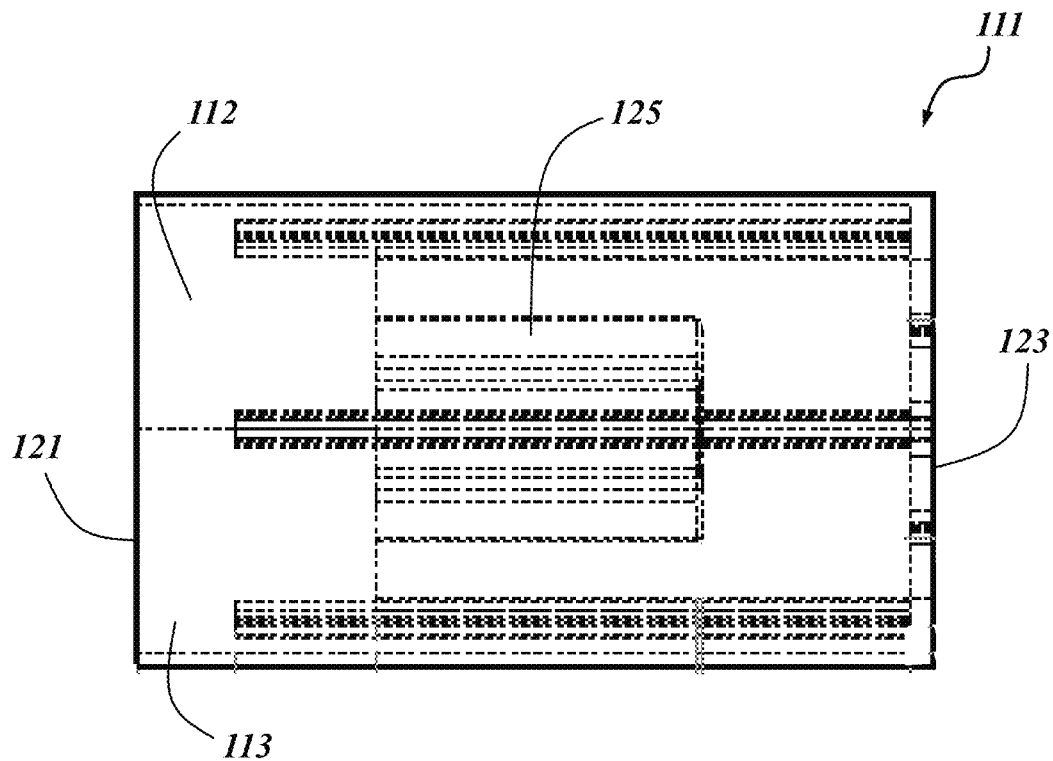

FIGS. 12-17 illustrate another embodiment of a bioreactor 110. The bioreactor 110 has an open-ended design and can be implemented in a number of different ways. The bioreactor 110 includes a body 111 that generally defines a culture chamber 112. The body 111 in this embodiment includes a first wall 113, a second wall 115, and a third wall 117, which are shown in FIGS. 12 and 13A. FIG. 13B illustrates a side view of the body 111 showing the first wall 113. The first wall 113 includes a first substrate 114; the second wall 112 includes a second substrate 116; and the third wall 117 includes a third substrate 119. The substrates 114, 116, 119 are removable and/or disposable plates in this embodiment, which can be employed with a reusable body. Alternatively, the substrates 114, 116, 119 may be integrally formed with the walls 113, 115, 117 of the body 111 or have another operable configuration. FIG. 12 shows an open end 121, and there is also a closed end 123 opposite the open end 121. Openings 125 within the interior of the body 111 are designed to mate with a cap 127, which is illustrated in FIGS. 14A and 14B. The illustrated embodiment includes three substrates 114, 116, 119 and three walls 113, 115, 117 which are arranged to form a polygonal-shaped culture chamber 112. The three substrates and walls form a triangle; however, it is possible to include more substrates and walls. For example, bioreactor bodies that includes four, five, six, seven, eight, or more than eight walls, to cite a few examples, are certainly possible. The number of substrates for culturing cell sources is preferably between one and eight. With more substrates, more complex shaped tissue constructs can be created, and larger volumes of tissues can be fabricated. A polygonal-shaped body, such as that shown in the figures, can be optimized to reduce the amount of media used in the culture chamber 112, which may lower the cost of culturing cell sources. The bioreactor 110 or its various components may be formed of an injection molded plastic to help reduce cost and encourage scalability, by assembling a number of bioreactors to a single manifold for feeding.

Figure 14A:
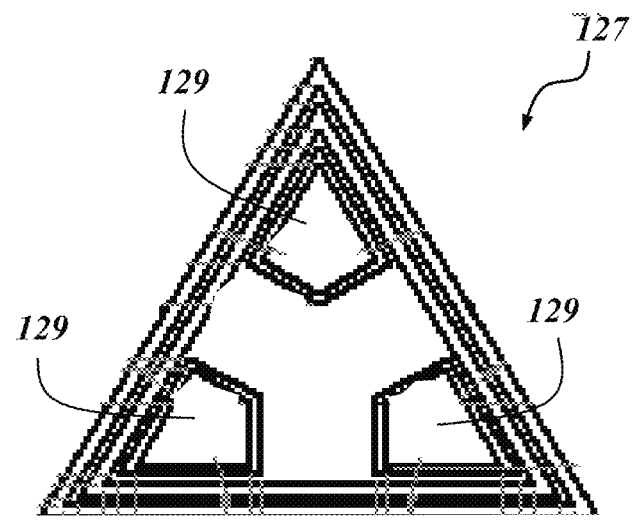
FIGS. 14A and 14B show various views of a cap that may be used for a bioreactor, such as the bioreactor shown in FIG. 12.
Figure 14B:
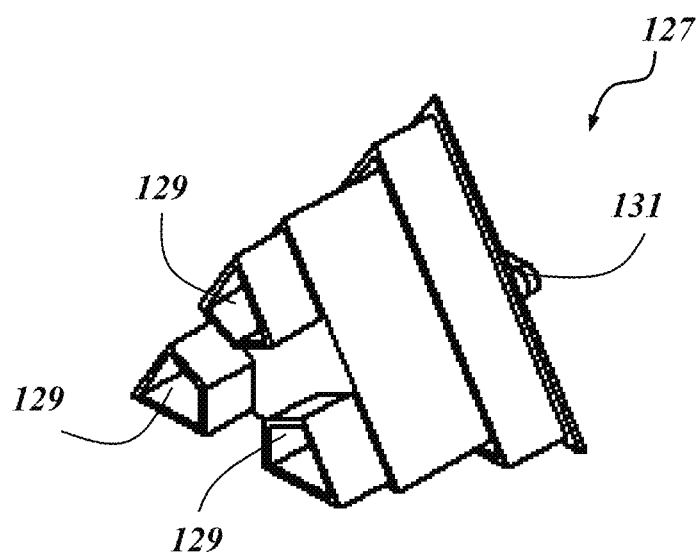

The bioreactor 110 may include a cap 127 to mate with the open end 121 of the body 111 to form a closed, sterile environment for cell culturing, as shown in FIGS. 14A and 14B. The cap 127 can have cap openings 129 which are designed to mate with the openings 125 of the body 111. Having the geometry of the cap 127 match or mimic the geometry of the body 111 can help reduce the amount of media needed. The cap 127 may have other features such as a handle 131 to help with placement and removal. It may also be possible to have a bioreactor with two open ends and a cap situated at either end. Silicone glue or vacuum grease may be used to help keep the system water and airtight. The body 111, the cap 127, and/or the substrate plates 114, 116, 119 may be formed of a transparent plastic material which allows a user to easily see cell growth on the substrates, when the tissue constructs translate and fuse in a desired position, and the final construct formation. Other features or components may be included with the body 111 and/or the cap 127 besides those illustrated in the figures. For example, a valve system may be used to help simultaneously grow and feed multiple tissue types with different types of media. One or more pressure release holes may be included for the displacement of gas when media is inserted into the culture chamber. Ports for the infusion and aspiration of cells and media that allow for near-complete aspiration of the media during media changes may be added. In one embodiment, corners of the bioreactor can be equipped with gates that regulate the flow of media between culture areas, thereby allowing for multiple types of media to be fed simultaneously to different cell monolayers.

Figure 15:
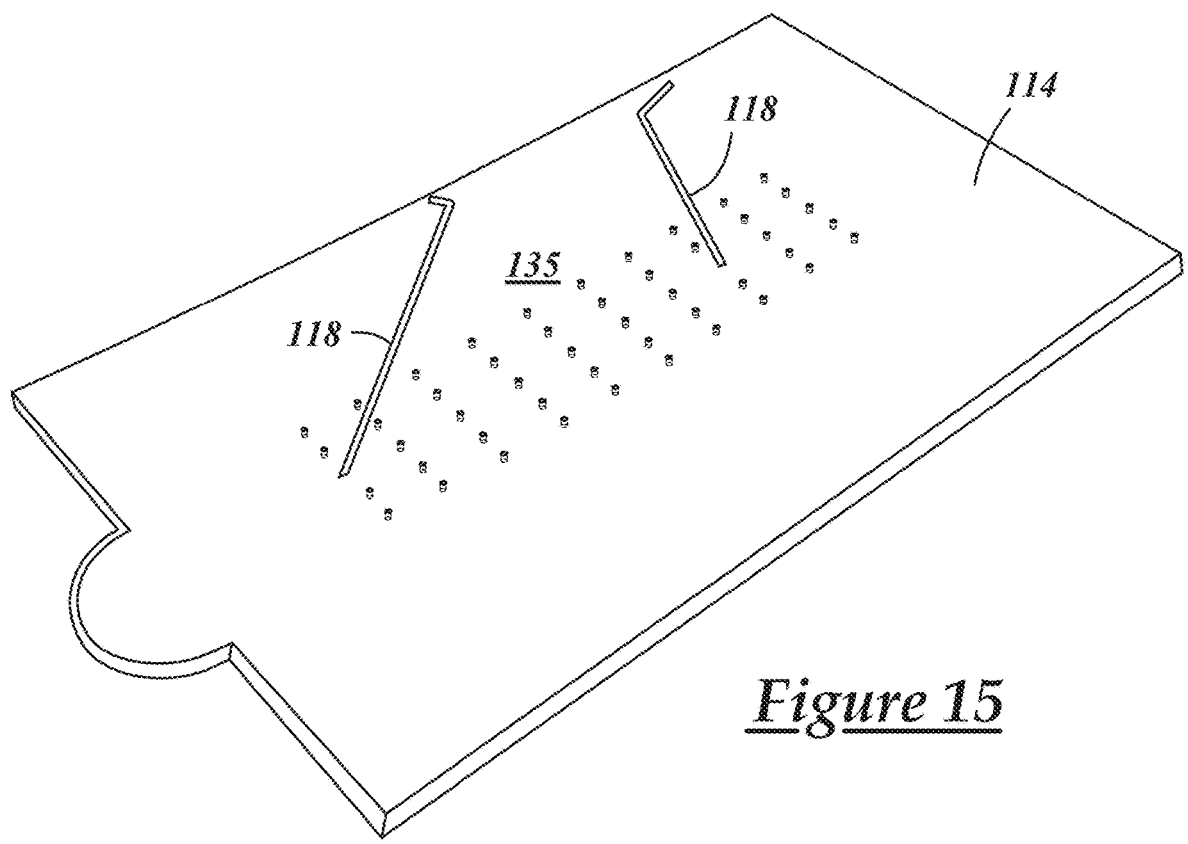
FIG. 15 shows translation mechanisms and a substrate that may be used with the bioreactor of FIG. 12.

With reference to FIGS. 12 and 15, bioreactor 110 includes one or more translation mechanisms 118. Preferably, each substrate 114, 116, 119 is equipped with translation mechanisms 118 in the form of pins which extend from a culture surface 135 toward a co-culture zone 133. In this embodiment, the co-culture zone 133 is centrally located in the culture chamber 112 between the three substrates 114, 116, 119, with translation mechanisms 118 extending from each respective substrate to the co-culture zone 133. In this embodiment, the co-culture zone is located remote from the substrates in the central portion of the bioreactor body 111; however, other locations for the co-culture zone are certainly possible. FIG. 15 shows translation mechanisms 118 in the form of a pair of angled pins, which may be similar to the embodiment shown and described with respect to FIGS. 4-6. More pins or translation mechanisms 118 may be included with each substrate, and each substrate may have a different configuration of translation mechanisms. Moreover, each substrate may include divots or openings to allow for insertion of pins in a number of locations. Divots may be preferred over holes in some embodiments, to help preserve the integrity of the surface 135 which may be formed of plasma treated polystyrene plastic. Additionally, each substrate can have a different size or geometry. For example, physical barriers such as multiple wells or a spatially optimized Teflon coating may be used. Other features such as a tab to assist with insertion and removal are certainly possible as well.

Figure 16A:
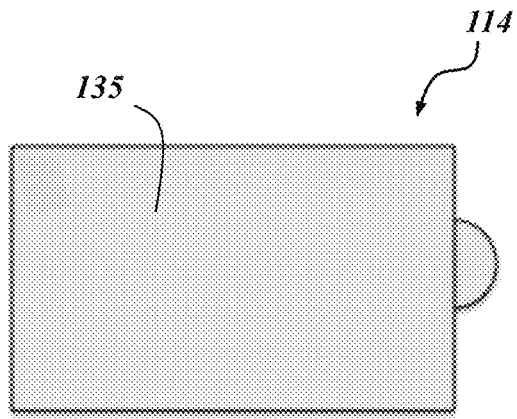
FIGS. 16A-16F illustrate various cell culture surfaces that may be used with bioreactor substrates.
Figure 16B:
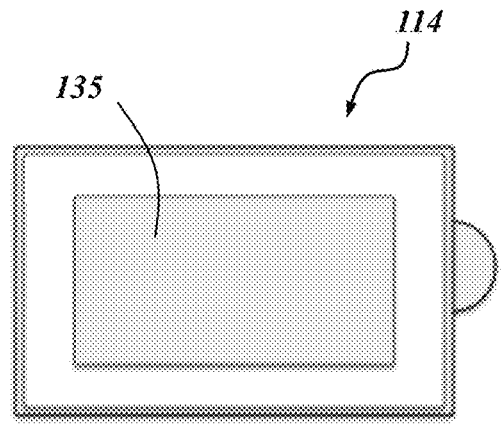
Figure 16C:
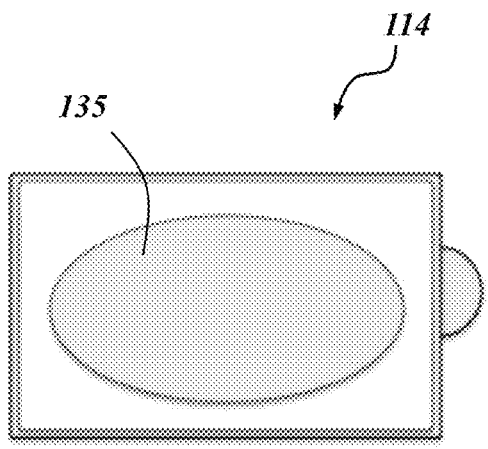
Figure 16D:
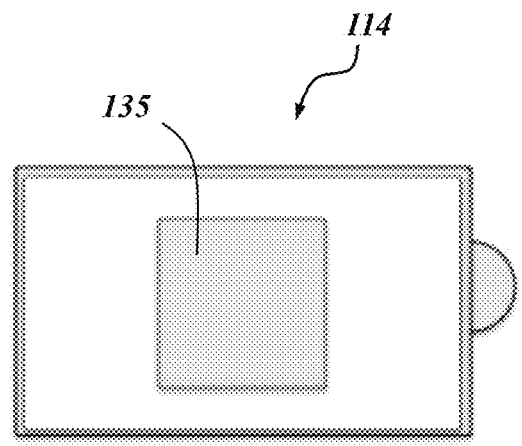
Figure 16E:
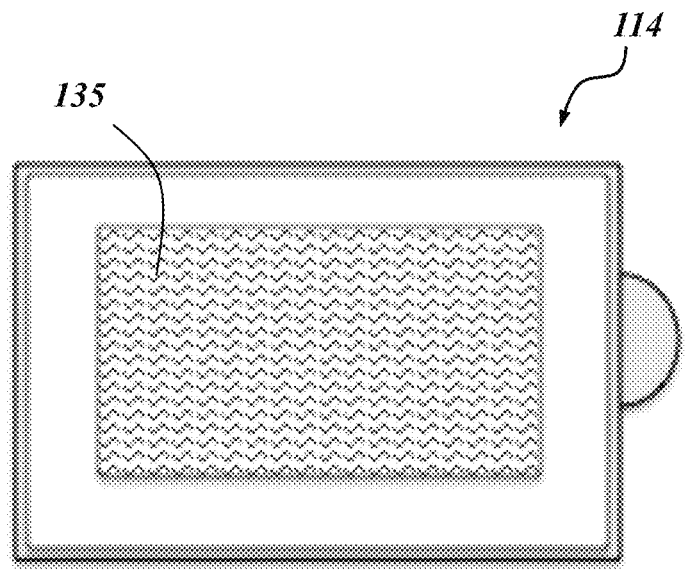
Figure 16F:
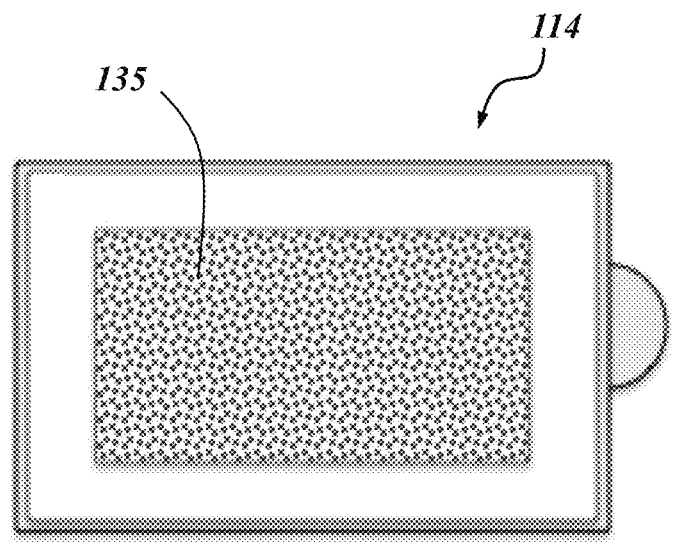

FIGS. 16A-16F illustrate various implementations for a substrate, such as substrate 114 with cell culture surface 135. In one embodiment, the substrate 114 is made from a plasma treated tissue plastic such as polystyrene. Plasma treated tissue plastic is used to allow the cells to adhere and proliferate to form a monolayer. The plastic sheets can be coated with either non-adherent coatings (e.g., silicone, Teflon, etc.), or adherent coatings (e.g., adhesion proteins, Matrigel, etc.). Different growth factors may also be used to coat the surface 135 to enhance the specificity of cell growth. The coating type and configuration can be manipulated to change the shape or cell type for adhesion to the surface of the plastic. FIG. 16A illustrates a plain cell culture surface 135. In FIG. 16B, the outer white areas are coated with Teflon. Because the cells will not adhere to Teflon, the coating on the cell surface 135 of this embodiment may be used to decrease the monolayer size. FIGS. 16C and 16D are similar to FIG. 16B, with an outer region coated in Teflon, but in these embodiments, the shape of the coating is altered to change the shape and size of the tissue construct to be formed. FIG. 16E includes a culture surface 135 that is coated with adhesion proteins to increase cell adhesion to adhere specific cell types. FIG. 16F shows a culture surface 135 that is coated with growth factors to enhance the growth of specific cells adherent to the substrate 114. Adhesion proteins and growth factors can be used alone or in combination to adhere and enhance the growth of adherent cells. Moreover, the bioreactor can include a number of different substrates having different coating configurations for each desired tissue construct to be formed, which ultimately impacts the multi-phasic or complex three-dimensional tissue construct.

Figure 17:
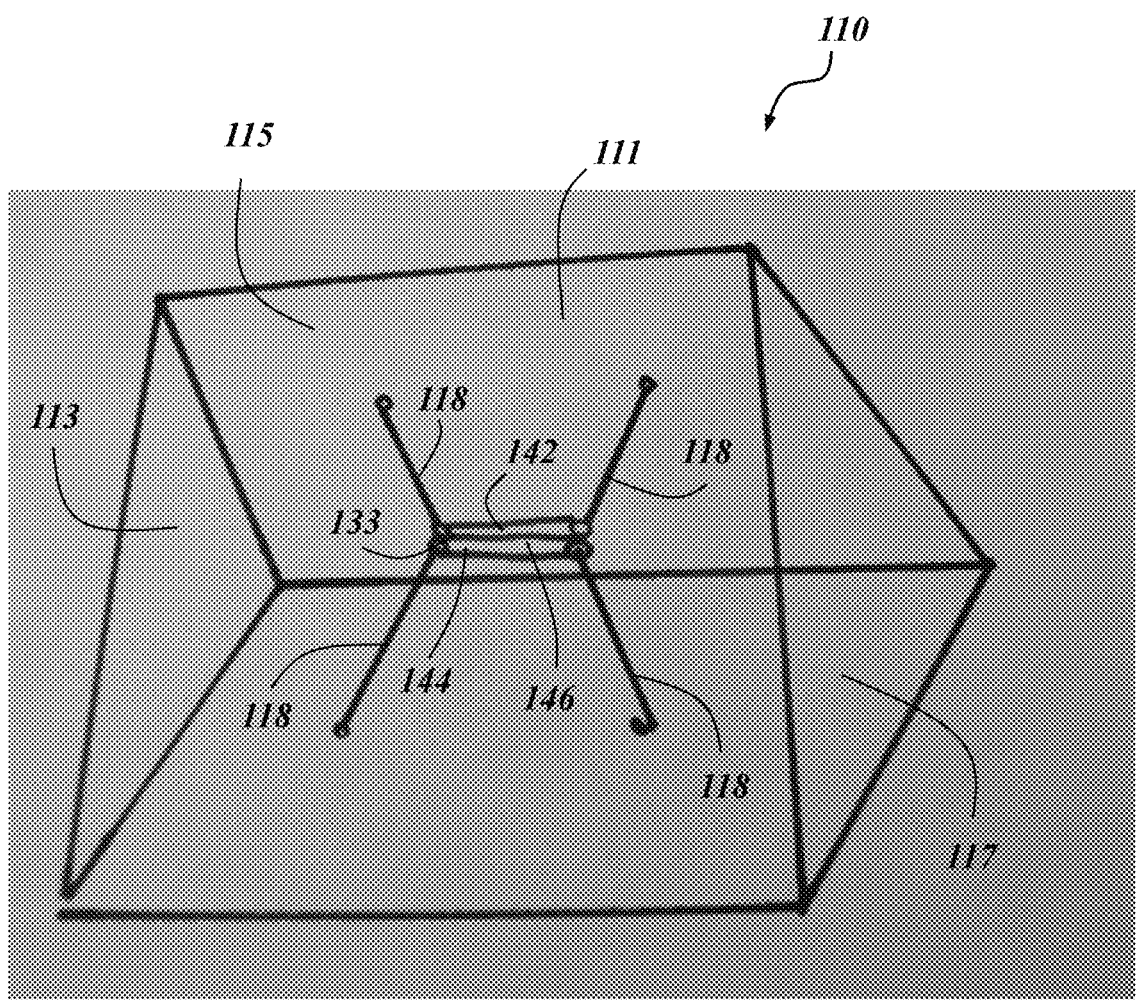
FIG. 17 schematically illustrates tissue construct formation in a bioreactor having a similar structure to the bioreactor depicted in FIG. 12.

FIG. 17 is a schematic illustration of the bioreactor 110. The translation mechanisms 118 in this embodiment are pins which are angled from 50 to 80 degrees, and preferably 70 degrees. In this embodiment, passive tension of each construct 142, 144 allows for the translation of each construct up each pin set toward the co-culture zone 133. The co-culture zone 133 can include interfacing or touching translation mechanisms 118, or the translation mechanisms may be spaced from each other to a certain extent. At the co-culture zone 133, the constructs 142, 144 fuse to form a complex three-dimensional tissue construct 146. A complex three-dimensional tissue construct includes two or more tissue constructs cultured from two or more cell sources. The cell sources may include the same cell type. In another embodiment, the complex three-dimensional tissue construct is a multi-phasic tissue construct which includes two or more tissue constructs cultured from two or more cell sources, with the cell sources having one or more different types of cells, such as the BLB construct described above. Applications of the formed constructs include repair of rotator cuff or anterior cruciate ligament injuries, to cite a few examples.

Figure 18:
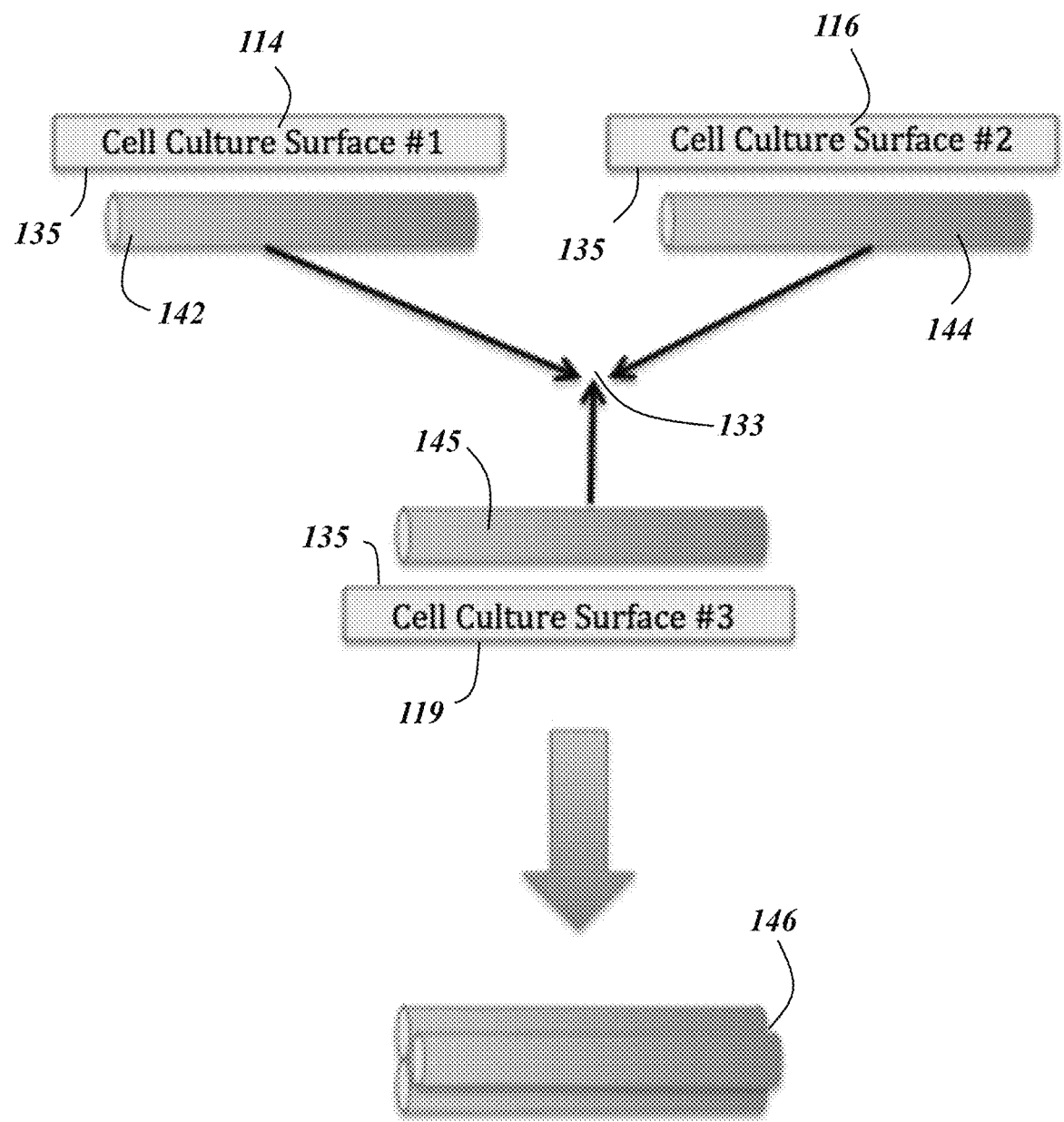
FIGS. 18 and 19 schematically represent tissue construct formation that is possible with the bioreactor shown in FIG. 12 in accordance with two embodiments.
Figure 19:
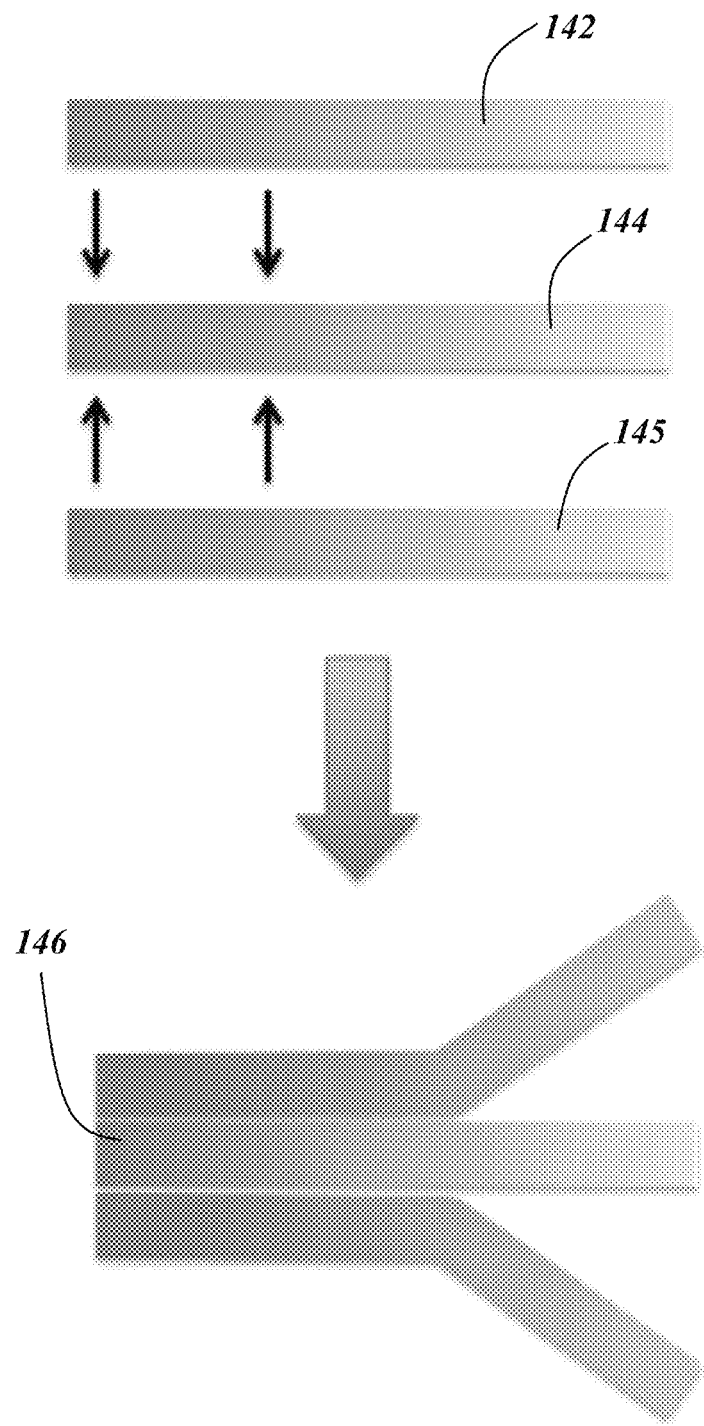

FIGS. 18 and 19 schematically represent various complex three-dimensional tissue constructs 146 that may be formed with the bioreactor 110. In FIG. 18, three tissue constructs 142, 144, 145 translate to the co-culture zone 133 to form a complex three-dimensional tissue construct 146 which is in column form. In FIG. 19, the three tissue constructs 142, 144, 145 may be formed with translation mechanisms 118 having particular configurations so as to allow translation of about one half of each construct to the co-culture zone. The translation mechanisms 118 may include hooks at the end to help stop the translation of the tissue construct at a certain point. The resulting complex three-dimensional tissue construct 146 has a three pronged configuration that may be used as a rotator cuff graft, for example.

Figure 20A:
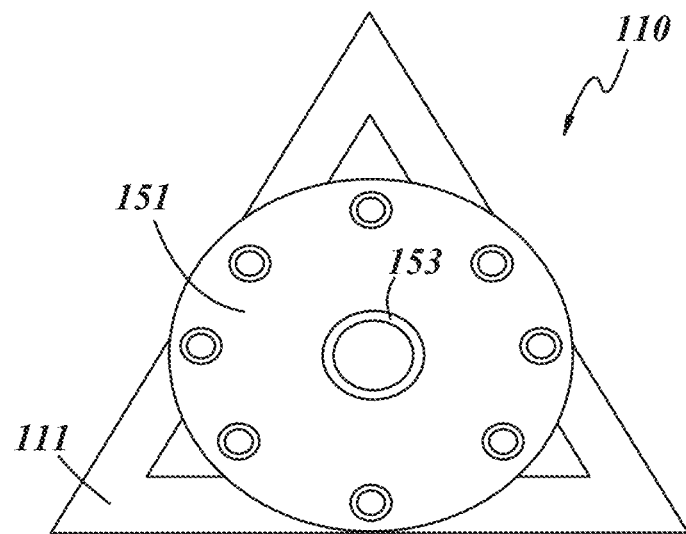
FIGS. 20A and 20B show various views of a rotary device that may be used with the bioreactor shown in FIG. 12.
Figure 20B:
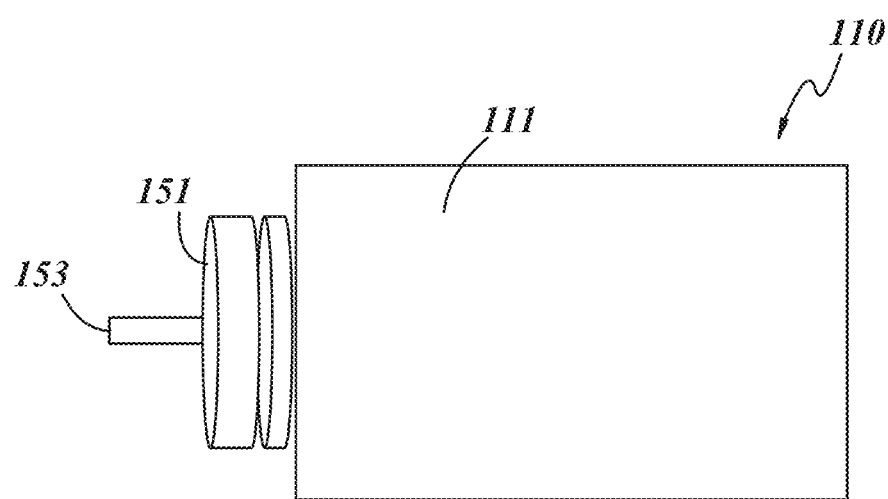
Figure 21:
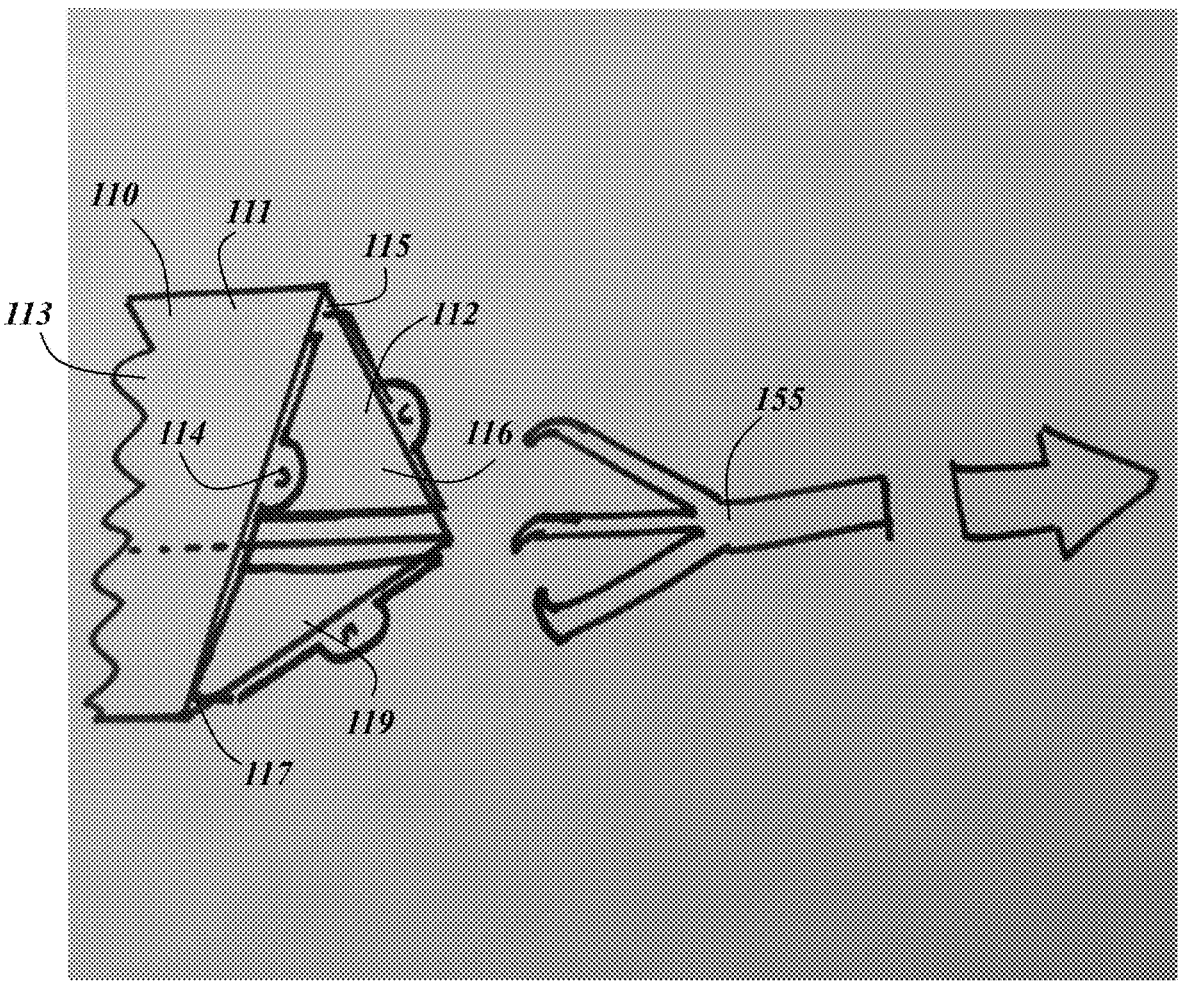
FIG. 21 illustrates a removing tool that may be used with the bioreactor shown in FIG. 12.
Figure 22:
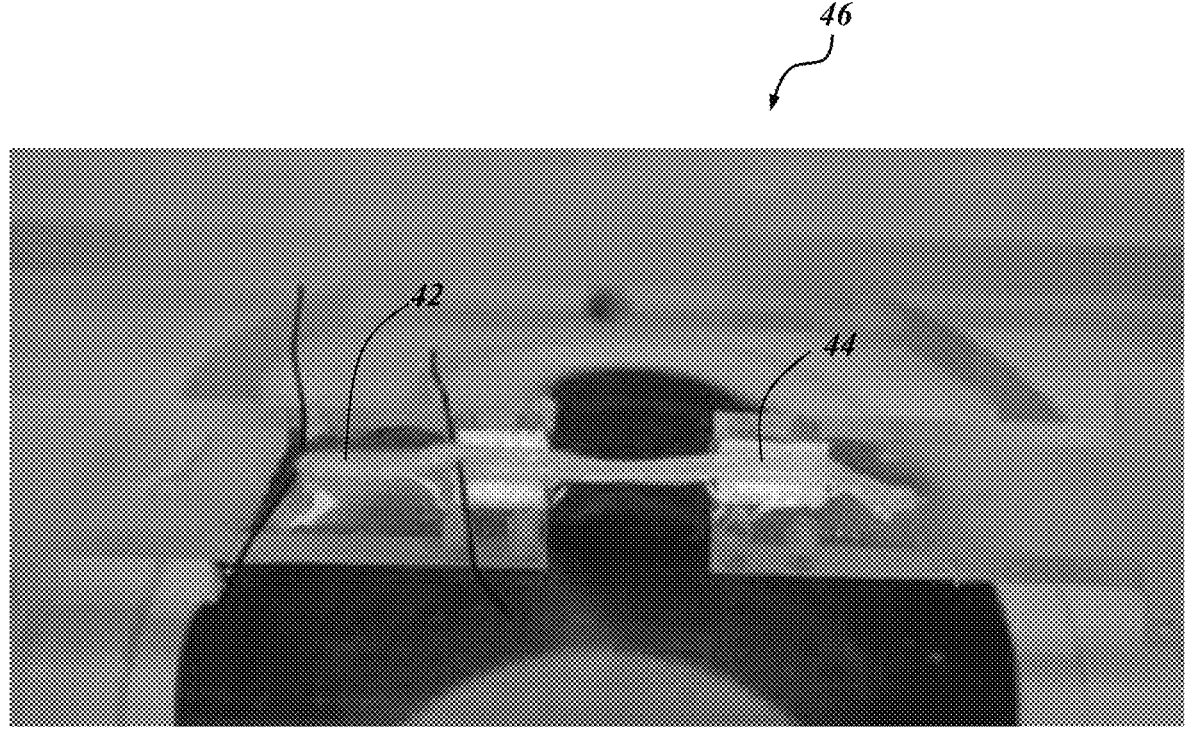
FIG. 22 is an image of a multi-phasic tissue construct formed in accordance with one embodiment and shown on a tensile test platform.

Other optional components for the bioreactor 110 are illustrated in FIGS. 20A, 20B, and 21, such as a rotary device 151 which allows the bioreactor 110 to be rotated about a rotary axis 153, and a grabbing device 155 which can help facilitate removal or insertion of the substrates 114, 116, 119. The rotary device 151 shown in FIGS. 20A and 20B can help allow for easy cell seeding, adherence of cells to the different substrates, and media changes. The grabbing device 155 depicted in FIG. 21 may be three-pronged as shown, or have a corresponding number of prongs depending on the number of walls and/or substrates of the bioreactor. All of the substrates 114, 116, 119 should be removed at the same time to avoid tearing the complex three-dimensional tissue construct. The grabbing device 155 can help grab and remove all three substrates at one time to harvest the tissue from the culture chamber 112.

FIGS. 22-25 illustrate various procedures that may be used to evaluate various qualities of a formed three-dimensional tissue construct. For the various exemplary procedures, a BLB multi-phasic tissue construct was removed from the bioreactor 10 and subjected to further evaluation. More particularly, separate parts of the construct were allocated for mechanical, histological, and molecular biology analysis. Approximately half of the bone/ligament construct was taken for histology and molecular biology testing. The rest was attached to a custom built tensile tester and submerged in DPBS for subsequent tensile testing. The tensile testing set-up can be seen in FIG. 22, which is an image of the described testing set-up of the ligament region 44 of the BLB construct 46. The missing bone region on the right, shown by the lack of sutures, indicates the region removed for PCR analysis. The construct was secured using custom Velcro grips and incrementally lengthened to approximate the original length within the bioreactor. Sixty-micron beads were painted onto the surface of the tissue for post analysis digital image correlation to extrapolate the tissue-level strain during testing. The construct 46 was pulled until failure at a rate of 0.01 strain/sec. The load and strain at failure was recorded.

Figure 23:
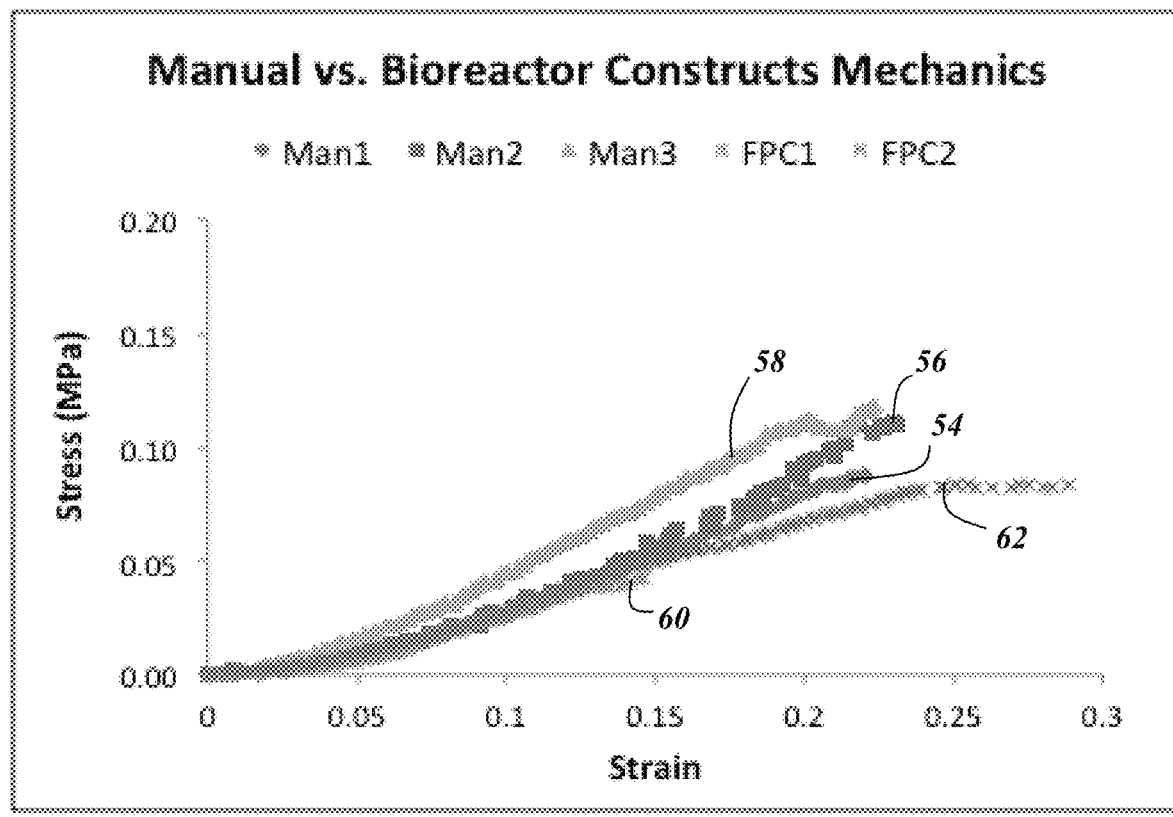
FIG. 23 is a graph showing stress-strain data of multi-phasic tissue constructs formed in accordance with various embodiments.

FIG. 23 is a graph showing stress-strain data of multi-phasic tissue constructs formed in accordance with various embodiments. Reference numerals 54, 56, 58 represent manually fabricated multi-phasic tissue constructs, and reference numerals 60, 62 represent bioreactor fabricated multi-phasic tissue constructs. Ligament constructs formed with a manual process, had a modulus of 0.38±0.12 MPa (n=3) at a physiological strain range of 0.05-0.07. The bioreactor constructs were similar, with an average tissue modulus of 0.28±0.09 MPa (n=2). The mechanics of the bone regions were not evaluated. The relative standard deviation within each group was approximately 30%. The diameter of the bioreactor constructs were 1.55±0.71 mm for BLBs (n=2) and 0.91±0.03 for ligament only constructs captured on pin plates (n=3).

For histological staining analysis, as shown in FIGS. 24A-24F, unfixed samples were placed into TBS medium (Triangle Biological Sciences), frozen in cold isopentane, and stored at −80 C until needed. Fixed samples were placed in 4% paraformaldehyde (PFA) for 1 hour. The sample was then placed into 15% sucrose solution for 1 hr at 4 C and then overnight (>12 hrs) in 30% sucrose solution also at 4 C. The constructs were then transferred into TBS medium, frozen over dry ice, and stored at −80 C until needed. Samples were cut to obtain cross and longitudinal sections with a cryostat at a thickness of 12 μm, adhered to Superfrost Plus microscopy slides and used for staining. Sections were stained for general morphology observations with hematoxylin and eosin (H&E). Mineral content of the tissue was determined via alizarin red staining (Sigma), and collagen with picro-sirius red stain. Alizarin red staining shows mineral nodules within the bone regions of the graft and absent from the ligament region of the graft, evidence of a bi-modal tissue distribution within the BLB graft, as shown in FIGS. 24A-24C. Mineralization was comparable to bone and ligament constructs culutred seperately in ostogenic and fibrogenic media respectively, demonstrating a capacity of the tissue to maintain its differntiated state while in co-culture. The construct was composed of primarily type 1 collagen and contained viable nuclei thoughout, as shown in FIGS. 24D-24F.

Figure 25:
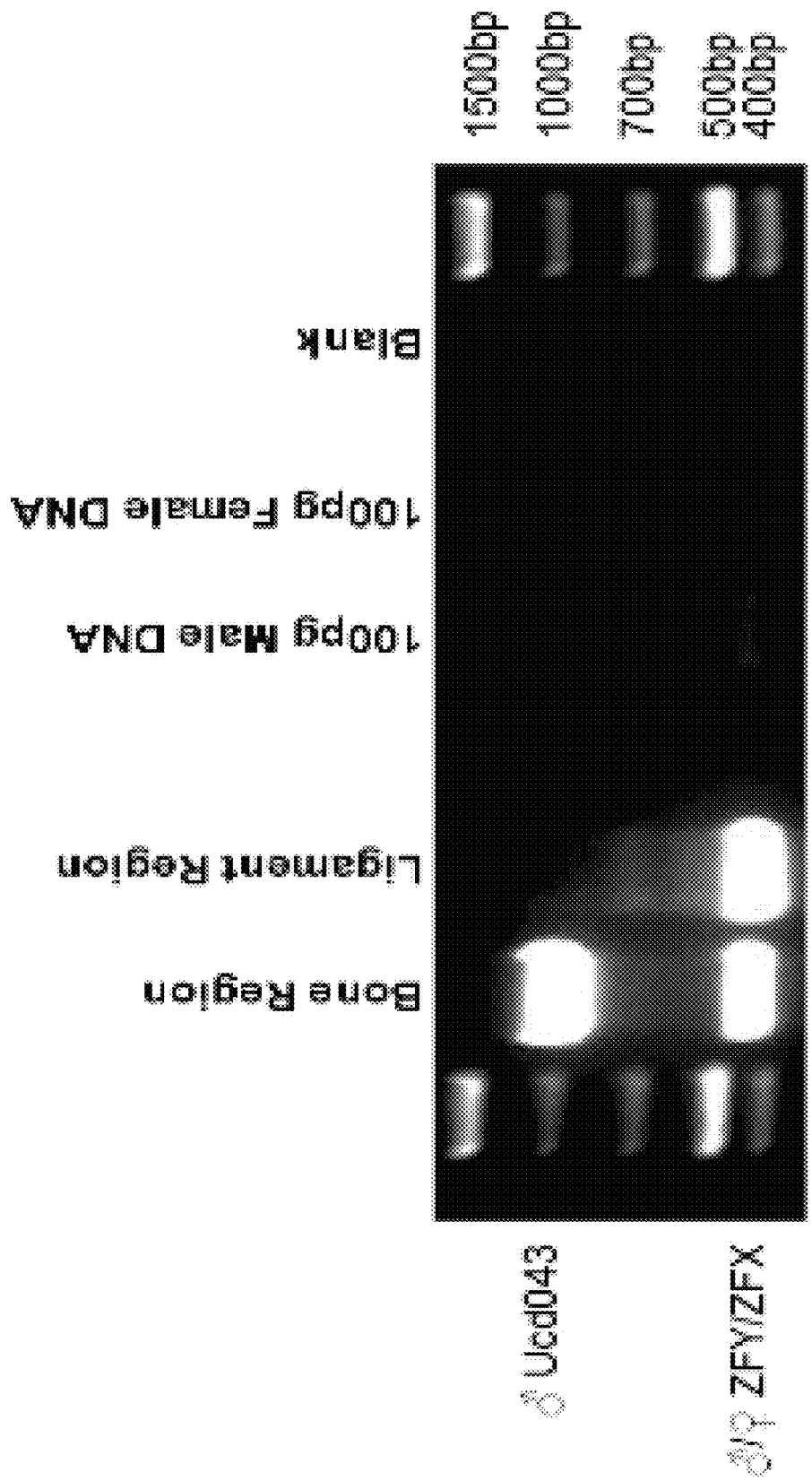
FIG. 25 illustrates polymerase chain reaction (PCR) data for a multi-phasic tissue construct formed in accordance with one embodiment.

With reference to FIG. 25, Y-chromosome PCR analysis was also performed. Genomic DNA was isolated from respective bone and ligament regions of the BLB tissue constructs by proteinase K digestion followed by ethanol precipitation. A PCR based assay for the ovine-specific Y-chromosome repeat sequence Ucd043 was used to determine the presence of male cells in BLB explant samples. Duplex PCR was performed using SCUcd043.FWD/SCUcd043. REV primers to amplify Ucd043 together with P1-5EZ/P2-3EZ primers to amplify the ZFY/ZFX locus. P1-5EZ and P2-3EZ primers also provided an internal control for amplification. Sensitivity of the assay was assessed with a dilution panel of 110 pg, 25 pg, and 5 pg of male ovine DNA. Subsequent experimental reactions were carried out with 25 ng of genomic DNA template. The PCR analysis demonstrates co-culture of multiple tissues within a continuous multi-phasic tissue construct. The male Y chromosome was detected in only bone regions of the construct, as shown in FIG. 25. Female tissue was detected throughout the construct and most highly expressed in central ligament region. Both the bone and ligament regions contained significant amounts of DNA.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A method of forming a multi-phasic tissue construct in a single culture chamber, comprising the steps of:
    forming a first tissue construct in the single culture chamber;
    translating the first tissue construct from a first substrate toward a second substrate via at least one translation mechanism that at least partially extends between the first substrate and the second substrate;
    adding cells to the single culture chamber containing the first tissue construct; and
    culturing the cells to form a second tissue construct in the single culture chamber, wherein the first tissue construct and the second tissue construct are formed from different cell types and together comprise the multi-phasic tissue construct.

2. The method of claim 1, wherein the cells are allogeneic mesenchymal stem cells (MSCs).

3. The method of claim 1, wherein the multi-phasic tissue construct includes muscle tissue, tendon tissue, nerve tissue, or some combination of one or more muscle tissue, tendon tissue, and nerve tissue.

4. The method of claim 1, wherein the first tissue construct is a bone tissue construct, the second tissue construct is a ligament tissue construct, and the multi-phasic tissue construct is a bone-ligament tissue construct.

5. The method of claim 4, wherein the culture chamber is at least partially divided into two culture vessels, and two bone tissue constructs are formed in each culture vessel of the culture chamber, and the ligament tissue construct extends between the two bone tissue constructs so that the multi-phasic tissue construct is a bone-ligament-bone (BLB) tissue construct.

6. The method of claim 1, wherein the step of adding cells takes place before the cells form a confluent tissue monolayer.

7. The method of claim 1, wherein the step of culturing the cells includes forming a spontaneously delaminating tissue monolayer.

8. The method of claim 1, wherein the first substrate and the second substrate comprise two walls of the culture chamber.

9. The method of claim 1, wherein the first tissue construct shrinks while translating away from the first substrate.

10. The method of claim 9, further comprising the step of translating the second tissue construct from the second substrate toward the first substrate via at least one translation mechanism that at least partially extends between the first substrate and the second substrate, wherein the second tissue construct shrinks while translating away from the second substrate.

11. A method of forming a complex three-dimensional tissue construct in a single culture chamber, comprising the steps of:
adding cells from a first cell source to a first substrate in the culture chamber;
adding cells from a second cell source to a second substrate in the culture chamber;
culturing the first cell source and the second cell source to form a first tissue construct and a second tissue construct;
translating the first and second tissue constructs via one or more translation mechanisms to a co-culture zone between the first and second substrates; and
forming the complex three-dimensional tissue construct having the second tissue construct of the second cell source cultured with the first tissue construct of the first cell source.

12. The method of claim 11, wherein the culture chamber includes a body for supporting the first substrate and the second substrate.

13. The method of claim 12, wherein the body is a polygonal-shaped body.

14. The method of claim 12, further comprising the step of removing the first substrate and the second substrate from the body of the culture chamber.

15. The method of claim 13, further comprising the step of reusing the body with new first and second substrates to form another complex three-dimensional tissue construct.

16. The method of claim 11, further comprising the step of using the culture chamber as a container for preservation, storage, and shipping of the complex three-dimensional tissue construct.

17. The method of claim 11, further comprising the step of adding cells from a third cell source to a third substrate in the culture chamber and culturing the cells of the third cell source with the first cell source and the second cell source to form the first tissue construct, the second tissue construct, and a third tissue construct, wherein the translating step includes translating the third tissue construct via the one or more translation mechanisms to the co-culture zone that is between the first, second, and third substrates, and forming the complex three-dimensional tissue construct having the third tissue construct of the third cell source cultured with the first and second tissue constructs of the first and second cell sources.

18. The method of claim 17, wherein the culture chamber includes a trigonal-shaped body for supporting the first substrate, the second substrate, and the third substrate.

\* \* \* \* \*